United States Patent [19]

Janulis et al.

[11] Patent Number: 5,399,291
[45] Date of Patent: Mar. 21, 1995

[54] LIQUID CRYSTAL COMPOUNDS HAVING A FLUOROETHER TERMINAL PORTION

[75] Inventors: Eugene P. Janulis, Mahtomedi; Gilbert C. Johnson, Lino Lakes; Marc D. Radcliffe, Woodbury; Patricia M. Savu, Maplewood; Daniel C. Snustad, Mendota Heights; Terence D. Spawn, Maplewood, all of Minn.

[73] Assignee: Minnesota Mining and Manufacturing Company, St. Paul, Minn.

[21] Appl. No.: 129,258

[22] Filed: Sep. 30, 1993

[51] Int. Cl.⁶ .................. C09K 19/52; C09K 19/30; C09K 19/32; G02F 1/13

[52] U.S. Cl. .................. 252/299.01; 252/299.61; 252/299.62; 252/299.63; 252/299.67; 544/298; 544/335; 546/270; 546/315; 546/322; 546/326; 549/369; 549/374; 549/380; 560/64; 560/65; 568/325; 568/331; 568/332; 568/642; 570/129; 359/104

[58] Field of Search .............. 252/299.01, 299.61, 252/299.62, 299.63, 299.64, 299.65, 299.66, 299.67; 544/298, 335; 546/270, 315, 322, 326; 549/369, 374, 180; 560/64, 65; 568/325, 331, 332, 642; 570/129; 359/104

[56] References Cited

U.S. PATENT DOCUMENTS

| 4,367,924 | 1/1983 | Clark et al. | 350/334 |
|---|---|---|---|
| 4,411,494 | 10/1983 | Crossland et al. | 350/339 R |
| 4,419,664 | 12/1983 | Crossland et al. | 340/784 |
| 4,528,562 | 7/1985 | Crossland et al. | 340/805 |
| 4,886,619 | 12/1989 | Janulis | 252/299.1 |
| 5,051,527 | 9/1991 | Suzuki et al. | 560/51 |
| 5,062,691 | 11/1991 | Tristani-Kendra et al. | 359/56 |
| 5,082,587 | 1/1992 | Janulis | 252/299.01 |
| 5,167,859 | 12/1992 | Wächtler et al. | 252/299.61 |
| 5,262,082 | 11/1993 | Janulis et al. | 252/299.01 |

FOREIGN PATENT DOCUMENTS

WO88/03530 5/1988 WIPO .......... C07D 239/26
WO91/00897 1/1991 WIPO .......... C09K 19/34

OTHER PUBLICATIONS

Abe, T., and S. Nagase; "Electrochemical Fluorination (Simons Process) as a Route to Perfluorinated Organic Compounds of Industrial Interest", *Preparation, Properties and Industrial Applications of Organofluorine Compounds*, 37-38 (1982).

Arnold, Z. and F. Sorm, Coll. Czech. Chem. Commun., 23, 452 (1958).

Clark, N. A. et al. (Appl. Phys. Lett. 36, 899 (1980)).

Holy., A., and Z. Arnold, Collection Czechoslov. Chem. Commun. 38, 1372 (1973).

Kahn, F. J., Appl. Phys. Lett. 22, 111 (1973).

Knunyants, I. L., L. Chih-yan and V. V. Shokina, Advances in Chem. (Uspekhi Khimi) 32, Original 1502, Eng. Trans. 461-76 (1963) Translation RSIC-165 (Redstone Information Center).

Lagerwall et al., 1st International Symposium on Ferroelectric Liquid Crystals, Bordeaux-Arcachon, France, 1987.

Meyer, R. B. et al., J. Physique 36, 1-69 (1975).

Miyasato et al., Jap. J. Appl. Phys. 22, 661 (1983).

Partridge, M. W., and W. F. Short, J. Chem. Soc., 390 (1947).

Pelzl et al., Kristall Technik. 14, 817 (1979).

Pelzl et al., Liquid Crystals 2, 21, 131 (1987).

Pelzl et al., Mol. Cryst. Liq. Cryst. 53, 167 (1979).

Zaschke, H. and Stolle, R., "Synthese niedrigschmelzender Kristallin-Flüssiger Hetercyclen; 5-n-Alkyl-2-[4-n-alkanoyloxy-phenyl]pyrimidine", Z. Chem. 15, 441-43 (1975).

*Primary Examiner*—Shean Wu
*Attorney, Agent, or Firm*—Gary L. Griswold; Walter N. Kirn; Lucy C. Weiss

[57] ABSTRACT

Fluorine-containing, chiral and achiral liquid crystal compounds comprise (a) an aliphatic fluorocarbon terminal portion comprising a perfluorinated or partially-fluorinated alkylene group and a terminal hydrocarbon alkyl group, the groups optionally containing at least one catenary ether oxygen atom; (b) an aliphatic hydrocarbon terminal portion; and (c) a central core connecting the terminal portions. The compounds have smectic mesophases or latent smectic mesophases and are useful, for example, in liquid crystal display devices.

24 Claims, No Drawings

LIQUID CRYSTAL COMPOUNDS HAVING A FLUOROETHER TERMINAL PORTION

FIELD OF THE INVENTION

This invention relates to fluorinated chiral and achiral smectic liquid crystal compounds. These compounds and mixtures of liquid crystal materials containing these compounds are useful in a variety of electrooptical displays.

BACKGROUND OF THE INVENTION

Devices employing liquid crystals have found use in a variety of electrooptical applications, in particular those which require compact, energy-efficient, voltage-controlled light valves, e.g., watch and calculator displays, as well as the flat-panel displays found in portable computers and compact televisions. Liquid crystal displays have a number of unique characteristics, including low voltage and low power of operation, which make them the most promising of the non-emissive electrooptical display candidates currently available. However, slow response and insufficient nonlinearity can impose limitations for many potential applications. The requirement for speed may become especially important in proportion to the number of elements which have to be addressed in a device. This limits the potential use of some types of liquid crystals.

The modes of liquid crystal displays that are most extensively employed at the present are twisted nematic (TN), supertwisted birefringence effect (SBE), and dynamic scattering (DS), all employing nematic or chiral nematic (cholesteric) liquid crystals. These devices are based upon the dielectric alignment effects (Freedericksz effect) of the nematic and/or chiral nematic liquid crystal (or mixtures of nematic or chiral nematic liquid crystals) upon application of an electric field. The average molecular long axis of the liquid crystal material takes up a preferred orientation in the applied electric field, the orientation of which is dependent on the sign of the dielectric anisotropy of the material or mixture, and this orientation relaxes upon removal of the applied electric field. This reorientation and relaxation is slow, on the order of a few milliseconds.

Although nematic and chiral nematic liquid crystals are the most extensively employed, there are liquid crystal devices that employ more highly ordered smectic liquid crystals. For example, materials with a smectic A mesophase are useful in device applications, as described by Crossland et al. in U.S. Pat. Nos. 4,411,494, 4,419,664, and 4,528,562, and by F. J. Kahn in Appl. Phys. Lett. 22, 111 (1973). These devices are based on the dielectric reorientation of the liquid crystals, and response times are on the order of milliseconds.

Mixtures which exhibit a chiral smectic A mesophase are also useful in device applications, as described by Lagerwall et al., 1st International Symposium On Ferroelectric Liquid Crystals, Bordeaux-Arcachon, France, 1987. These mixtures exhibit an electrooptic effect which is termed a soft-mode ferroelectric effect, and sub-microsecond switching can be achieved.

Materials with a smectic C mesophase are useful in device applications, as described by Pelzl et al. in Kristall Technik. 14, 817 (1979), Mol. Cryst. Liq. Cryst. 53, 167 (1979), and Liquid Crystals 2, 21, 131 (1987). These devices are based on the dielectric reorientation of the liquid crystals, and the response times are slow.

A recent advance in the liquid crystal art has been the utilization of tilted chiral smectic liquid crystals, which are also termed ferroelectric liquid crystals, in devices which give microsecond switching and bistable operation not possible in any of the device applications described above. Ferroelectric liquid crystals were discovered by R. B. Meyer et al. (J. Physique 36, 1–69 (1975)). A high speed optical switching phenomenon was discovered for the ferroelectric liquid crystals by N. A. Clark et al. (Appl. Phys. Lett. 36, 899 (1980) and U.S. Pat. No. 4,367,924).

Fluorine-containing ferroelectric liquid crystal materials have recently been developed. U.S. Pat. No. 4,886,619 (Janulis) discloses fluorine-containing, chiral smectic liquid crystal compounds which comprise a fluorocarbon terminal portion and a chiral hydrocarbon terminal portion, the terminal portions being connected by a central core. U.S. Pat. No. 5,082,587 (Janulis) discloses achiral, fluorine-containing liquid crystal compounds which comprise a fluorocarbon terminal portion and a hydrocarbon or another fluorocarbon terminal portion, the terminal portions being connected by a central core. U.S.S.N. 07/875223 now U.S. Pat. No. 5,262,082 (Janulis et al.) describes achiral, fluorine-containing liquid crystal compounds comprising an aliphatic fluorocarbon terminal portion having at least one catenary ether oxygen and an aliphatic hydrocarbon terminal portion, the terminal portions being connected by a central core.

International Publication Nos. WO 88/03530 (Merck) and WO 91/00897 (Merck) disclose chiral or achiral ring compounds which may be used as components of chiral, tilted, smectic liquid-crystalline phases with ferroelectric properties.

The high speed switching of the ferroelectric liquid crystals can be utilized in many applications, e.g., light valves, displays, printer heads, and the like. In addition to the microsecond switching speeds, some ferroelectric liquid crystal device geometries exhibit bistable, threshold-sensitive switching, making them candidates for matrix-addressed devices containing a large number of elements for passive displays of graphic and pictorial information, as well as optical processing applications.

SUMMARY OF THE INVENTION

Briefly, in one aspect, this invention provides fluorine-containing, chiral and achiral liquid crystal compounds having smectic mesophases or latent smectic mesophases. (Compounds having latent smectic mesophases are those which by themselves do not exhibit a smectic mesophase, but which, when in admixture with compounds having smectic mesophases or with other compounds having latent smectic mesophases, develop smectic mesophases under appropriate conditions.) The compounds of the invention comprise (a) an aliphatic fluorocarbon terminal portion comprising a perfluorinated or partially-fluorinated alkylene group and a terminal hydrocarbon alkyl group, the groups optionally containing at least one catenary, i.e., in-chain, ether oxygen atom; (b) an aliphatic hydrocarbon terminal portion; and (c) a central core connecting the terminal portions. The aliphatic fluorocarbon terminal portion can be represented by the formula $-D-R_f-R_h$, wherein D is selected from the group consisting of a covalent bond,

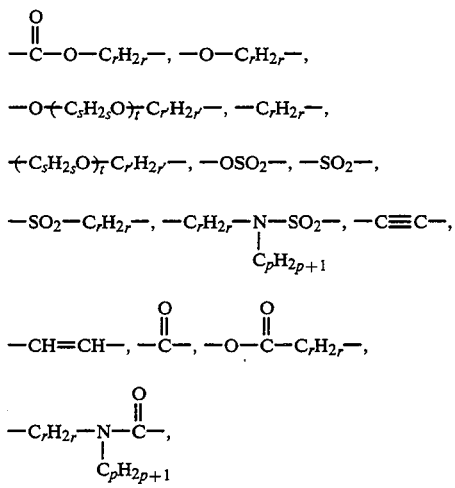

where r and r' are independently integers of 1 to about 20, s is independently an integer of 1 to about 10 for each ($C_sH_{2s}O$), t is an integer of 1 to about 6, and p is an integer of 0 to about 4; $R_f$ is a linear or branched, perfluorinated or partially-fluorinated alkylene group having from 1 to about 10 (preferably, from about 2 to about 6) carbon atoms and optionally containing one or more catenary ether oxygen atoms; and $R_h$ is a linear or branched alkyl group having from 1 to about 14 (preferably, from about 3 to about 10) carbon atoms and optionally containing one or more catenary ether oxygen atoms. Preferably, $R_f$ is perfluorinated, both $R_h$ and $R_f$ are linear, and at least one of the groups $R_h$ and $R_f$ contains at least one catenary ether oxygen atom. Most preferably, $R_h$ or both $R_h$ and $R_f$ contains at least one catenary ether oxygen atom.

In general, the compounds of this invention have a central core comprised of at least one or two rings independently selected from the group consisting of aromatic, heteroaromatic, alicyclic, substituted aromatic, substituted heteroaromatic, and substituted alicyclic rings, the rings being connected one with another by a covalent bond or by chemical groups selected from the group consisting of —COO—, —COS—, —HC=N—, —HC=CH—, and —COSe—. The rings can be fused or non-fused. The heteroatoms within the heteroaromatic rings comprise at least one atom selected from the group consisting of nitrogen, oxygen, and sulfur. Non-adjacent methylene groups in the alicyclic rings can be substituted by oxygen or sulfur atoms.

The chiral liquid crystal compounds of the present invention are optically active (except when in the form of a racemic mixture) and are useful alone or in admixture with other chiral or achiral liquid crystal compounds for electrooptical display applications. The achiral compounds of the invention are not optically active but are useful, for example, when placed in admixture with the chiral compounds of the invention or with other liquid crystal materials, e.g., ferroelectric liquid crystal compounds having perfluoroaliphatic terminal portions such as those compounds disclosed, for example, in U.S. Pat. Nos. 4,886,619 and 5,082,587 (Janulis). The compounds of the invention, in general, possess a lower temperature smectic A phase than compounds having aliphatic or perfluoroaliphatic terminal portions with or without an ether linkage and with substantially the same number of carbon atoms in the terminal portion.

The liquid crystal compounds of the invention when used in admixture with ferroelectric liquid crystal compounds having perfluoroaliphatic or perfluoroether terminal portions act to suppress the formation of higher order mesophases or crystallinity, relative to the same compositions without the liquid crystal compounds of the invention. This is important because a device containing such a mixture will function only in the desired smectic C phase of the mixture. Once the liquid crystals in the device have gone to higher order, it is difficult to get uniform alignment back, and the device is rendered useless.

The fluorine-containing liquid crystal compounds of the invention also have good chemical stability toward water, weak acids, and weak bases; do not undergo degradation during normal use in a liquid crystal display device; and are photochemically stable, i.e., do not easily undergo photochemical reactions. Many of these compounds, due to the novel aliphatic fluorocarbon terminal portion, have enhanced smectogenic properties and lower birefringences than their non-fluorine-containing analogues. The compounds, and mixtures which contain them, are useful in a variety of electrooptical displays. In particular, these fluorinated materials exhibit smectic mesophases, especially smectic A, and are useful in the formulation of nematic, chiral nematic, i.e., cholesteric, smectic A (SmA), smectic C (SmC), chiral smectic A (SmA*), and chiral smectic C (SmC*) mixtures.

In other aspects, this invention also provides a mixture of liquid crystal compounds comprising at least one liquid crystal compound of the invention, intermediates useful in the preparation of the liquid crystal compounds of the invention, and a liquid crystal display device containing at least one liquid crystal compound of the invention.

DETAILED DESCRIPTION OF THE INVENTION

The achiral liquid crystal compounds of the present invention can be represented by the general formula I:

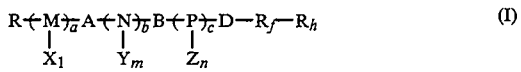  (I)

where M, N, and P are each independently selected from the group consisting of

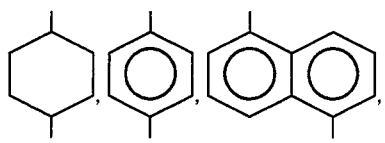

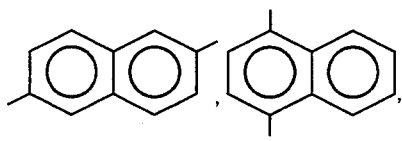

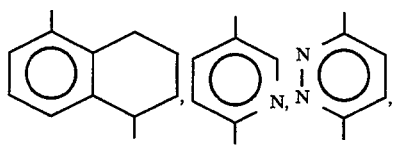

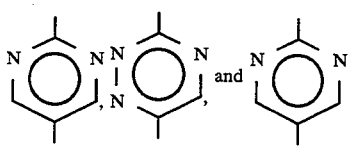

a, b, and c are each independently zero or an integer of from 1 to 3, with the proviso that the sum of a+b+c be at least 1;

each A and B are non-directionally and independently selected from the group consisting of a covalent bond,

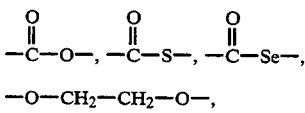

$-(CH_2CH_2)_k-$ where k is 1 to 4, $-CH=CH-$, $-C\equiv C-$, $-CH=N-$, $-CH_2-O-$,

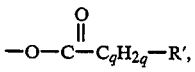

and $-O-$;

each X, Y, and Z are independently selected from the group consisting of $-H$, $-Cl$, $-F$, $-Br$, $-I$, $-OH$, $-OCH_3$, $-CH_3$, $-CF_3$, $-OCF_3$, $-CN$, and $-NO_2$;

each l, m, and n are independently zero or an integer of 1 to 4;

D is selected from the group consisting of a covalent bond,

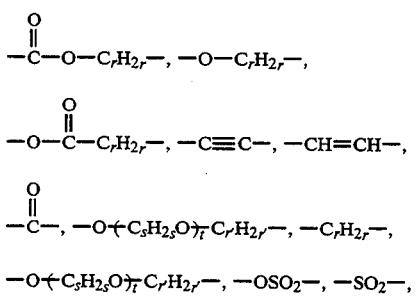

$-SO_2-C_rH_{2r}-$, $-C_rH_{2r}-N(C_pH_{2p+1})-SO_2-$, $-C_rH_{2r}-N(C_pH_{2p+1})-C(O)-$, and combinations thereof, where r and r' are independently integers of 1 to about 20, s is independently an integer of 1 to about 10 for each $(C_sH_{2s}O)$, t is an integer of 1 to about 6, and p is an integer of 0 to about 4;

R is selected from the group consisting of

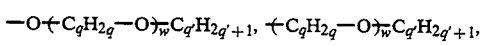

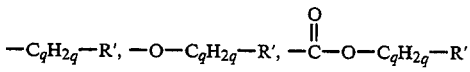

and

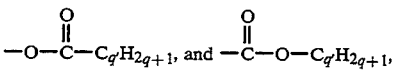

where R' is selected from the group consisting of $-Cl$, $-F$, $-CF_3$, $-NO_2$, $-CN$, $-H$, $-O-C(O)-C_qH_{2q+1}$, and $-C(O)-O-C_qH_{2q+1}$, where q and q' are independently integers of 1 to about 20, w is an integer of 1 to about 10, and R can be linear or branched;

$R_f$ is a linear or branched, perfluorinated or partially-fluorinated alkylene group having from 1 to about 10 (preferably, from about 2 to about 6) carbon atoms and optionally containing one or more catenary ether oxygen atoms;

and $R_h$ is a linear or branched alkyl group having from 1 to about 14 (preferably, from about 3 to about 10) carbon atoms and optionally containing one or more catenary ether oxygen atoms. Preferably, $R_f$ is perfluorinated, both $R_h$ and $R_f$ are linear, and at least one of the groups $R_h$ and $R_f$ contains at least one catenary ether oxygen atom.

The chiral liquid crystal compounds of the present invention can also be represented by the general formula I supra, wherein M, N, P, A, B, X, Y, Z, a, b, c, l, m, n, D, $R_f$, and $R_h$ are as defined above for the achiral compounds, and R is selected from the group defined above with the proviso that R is chiral.

Preferred classes of the achiral compounds of the invention can be represented by the following formulas:

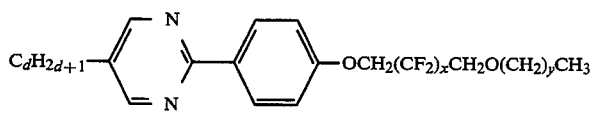

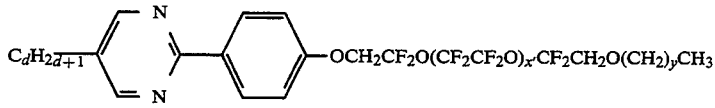

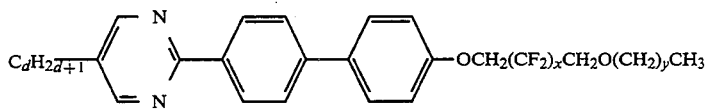
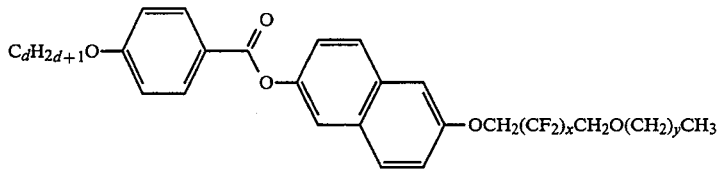
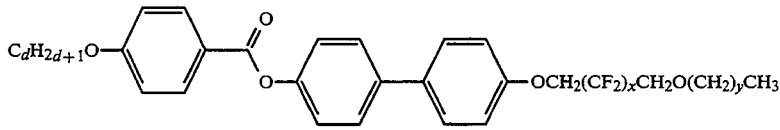
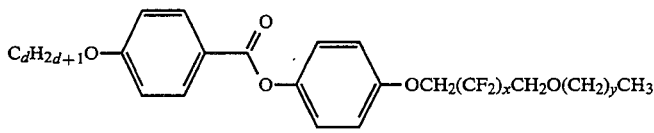
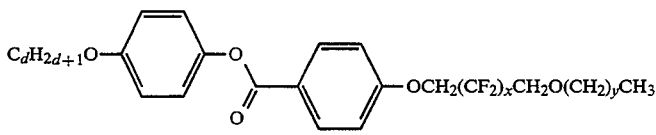
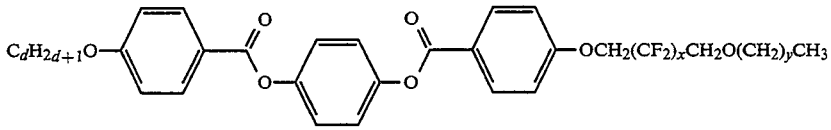
and preferred classes of the chiral compounds of the invention can be represented by the following formulas:
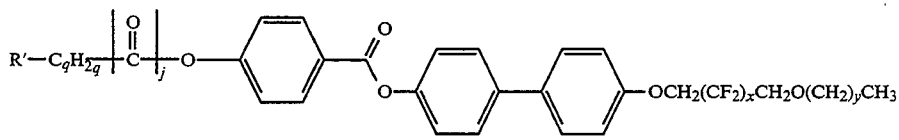
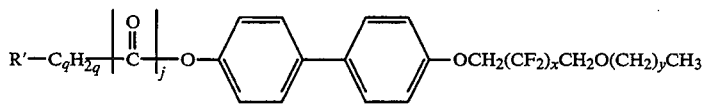
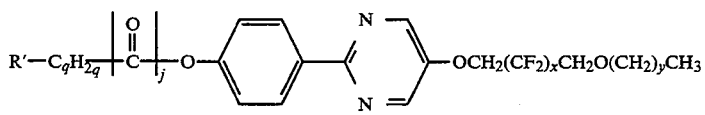
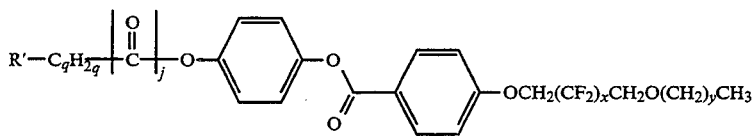

-continued

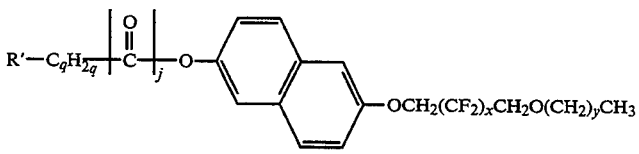

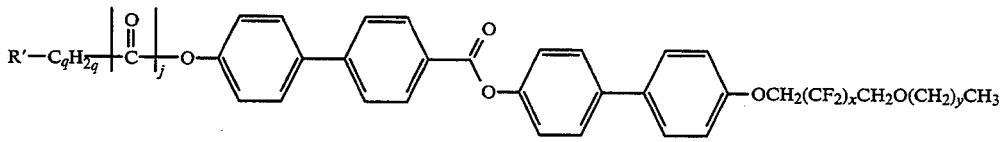

where d is an integer of about 4 to about 10, x is an integer of 1 to about 10, y is an integer of 1 to about 12, x' is an integer of 0 to about 4, j is an integer of 0 or 1, q is an integer of 2 to about 10, R' is selected from the group consisting of hydrogen, fluorine, chlorine, and perfluoromethyl; and $C_qH_{2q}$ can be linear or branched.

The compounds of the present invention have birefringences typically in the range of 0.05–0.18 depending on the ring systems present and the number of rings, have suppressed nematic mesophases (i.e., exhibit no or very small nematic mesophase temperature ranges), and have enhanced smectic mesophases. Mixtures of the compounds of the invention with other liquid crystal materials can be formulated to provide desired transition temperatures and broad mesophase temperature ranges. Such mixtures preferably contain the fluorine-containing, chiral smectic liquid crystal compounds described in U.S. Pat. No. 4,886,619 (Janulis) and/or the fluorine-containing, achiral liquid crystal compounds described in U.S. Pat. No. 5,082,587, the descriptions of which are incorporated herein by reference.

The individual compounds of this invention which exhibit smectic A behavior can be used in admixture with other materials in smectic A device applications (as described by Crossland et al. in U.S. Pat. Nos. 4,411,494, 4,419,664, and 4,528,562, the descriptions of which are incorporated herein by reference, and by F. J. Kahn in Appl. Phys. Lett. 22, 111 (1973)).

The individual compounds of this invention can be used in admixture with other materials in the smectic C Freedericksz device application described by Pelzl et al., (see Kristall Technik. 34, 817 (1979); Mol. Cryst. Liq. Cryst. 53, 167 (1979); and Liquid Crystals 2, 21, 131 (1987)).

An advantage of using the materials of this invention in the formulation of liquid crystal mixtures is the low birefringence which can be obtained. The low birefringence of the liquid crystal compounds of the invention (relative to their non-fluorine-containing analogues) allows the fabrication of devices with larger device spacings. Light transmission through, e.g., a surface-stabilized ferroelectric device (as described in U.S. Pat. No. 4,367,924, the description of which is incorporated by reference herein) with two polarizers is represented by the following equation:

$I = I_o (sin^2(4\Theta)) (sin^2(\pi \Delta nd/\lambda))$ where $I_o$ = transmission through parallel polarizers
$\Theta$ = material tilt angle
$\Delta n$ = liquid crystal birefringence
d = device spacing
$\lambda$ = wavelength of light used To maximize the transmission, both $sin^2(4\Theta)$ and $sin^2(\pi \Delta nd/\lambda)$ must be at maximum. This occurs when each term equals one. The first term is a maximum when the tilt angle equals 22.5°. This is a function of the liquid crystal and is constant for a given material at a given temperature. The second term is maximum when $\Delta nd = \lambda/2$. This demonstrates the criticality of the low birefringence of the materials of this invention. Low birefringence allows a larger device thickness, d, for a given wavelength of light. Thus, a larger device spacing is possible while still maximizing transmission, allowing easier device construction.

The fluorine-containing liquid crystal compounds of the invention can be prepared by a process comprising the steps of (1) mixing at least one compound represented by the formula

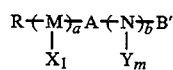

with at least one compound represented by the formula

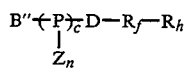

or (2) mixing at least one compound represented by the formula

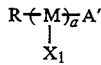

with at least one intermediate compound represented by the formula

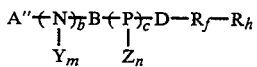

where M, N, and P are each independently selected from the group consisting of

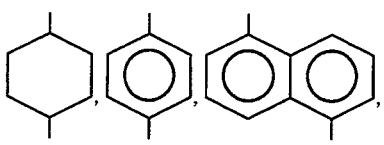

-continued

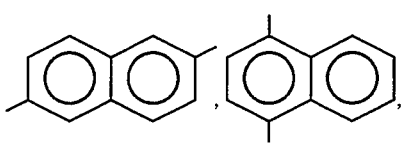

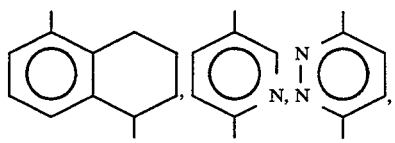

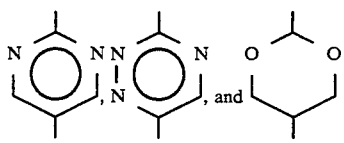

a, b, and c are each independently zero or an integer of from 1 to 3, with the proviso that the sum of a+b+c be at least 1;

each A and B are non-directionally and independently selected from the group consisting of a covalent bond, $$-\overset{O}{\underset{\|}{C}}-O-, \quad -\overset{O}{\underset{\|}{C}}-S-, \quad -\overset{O}{\underset{\|}{C}}-Se-,$$

$$-O-CH_2-CH_2-O-, \quad -O-\overset{O}{\underset{\|}{C}}-CH_2-O-,$$

$$-\overset{O}{\underset{\|}{C}}-Te-,$$

$-(CH_2CH_2)_k-$ where k is 1 to 4, $$-\overset{O}{\underset{\|}{C}}-,$$

and —O—; each A', A", B', and B" are independently selected from the group consisting of —OH, —COOH, —CH(CH$_2$OH)$_2$, —SH, —SeH, —the, —NH$_2$, —COCl, —CHO, —OSO$_2$R$_f'$, and —CH$_2$COOH (preferably, —OSO$_2$R$_f'$), where R$_f'$ is a perfluoroalkyl group having from 1 to about 10 carbon atoms, and with the proviso that A' can enter into an addition or condensation reaction with A" and that B' can enter into an addition or condensation reaction with B";

each X, Y, and Z are independently selected from the group consisting of —H, —Cl, —F, —Br, —I, —OH, —OCH$_3$, —CH$_3$, —CF$_3$, —OCF$_3$ —CN, and —NO$_2$;

each l, m, and n are independently zero or an integer of 1 to 4;

D is selected from the group consisting of a covalent bond, $$-\overset{O}{\underset{\|}{C}}-O-C_rH_{2r}-, \quad -O-C_rH_{2r}-, \quad -O-\overset{O}{\underset{\|}{C}}-C_rH_{2r}-,$$

$$-C\equiv C-, \quad -CH=CH-, \quad -\overset{O}{\underset{\|}{C}}-,$$

$-O(-C_sH_{2s}O)_t C_rH_{2r}-, \quad -C_rH_{2r}-,$ $-C_sH_{2s}O(-C_rH_{2r})_t, \quad -OSO_2-, \quad -SO_2-,$ -continued $-SO_2-C_rH_{2r}-, \quad -C_rH_{2r}-\overset{}{\underset{C_pH_{2p+1}}{N}}-SO_2-,$ $-C_rH_{2r}-\overset{}{\underset{C_pH_{2p+1}}{N}}-\overset{O}{\underset{\|}{C}}-,$ and combinations thereof, where r and r' are independently integers of 1 to about 20, s is independently an integer of 1 to about 10 for each (C$_s$H$_{2s}$O), t is an integer of 1 to about 6, and p is an integer of 0 to about 4;

R is selected from the group consisting of

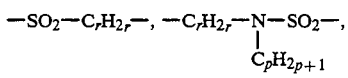

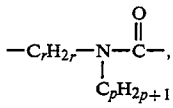

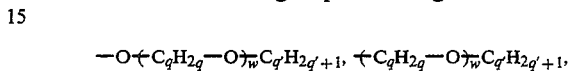

and

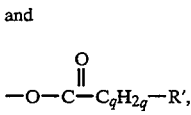

where R' is selected from the group consisting of —Cl, —F, —CF$_3$, —NO$_2$, —CN, —H,

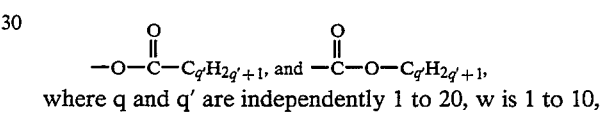

where q and q' are independently 1 to 20, w is 1 to 10, and R can be linear or branched;

R$_f$ is a linear or branched, perfluorinated or partially-fluorinated alkylene group having from 1 to about 10 (preferably, from about 2 to about 6) carbon atoms and optionally containing one or more catenary ether oxygen atoms;

and R$_h$ is a linear or branched alkyl group having from 1 to about 14 (preferably, from about 3 to about 10) carbon atoms and optionally containing one or more catenary ether oxygen atoms;

and allowing said A' and A" or B' and B" to react in the presence of suitable coupling agents, i.e., a reagent which effects coupling.

Objects and advantages of this invention are further illustrated by the following examples, but the particular materials and amounts thereof recited in these examples, as well as other conditions and details, should not be construed to unduly limit this invention.

In the following examples, all temperatures are in degrees Centigrade and all parts and percentages are by weight unless indicated otherwise. Commercially available materials were chemically transformed by reaction pathways well-known to those skilled in the art and detailed in the examples. Chemical transformations were comprised of acylation, esterification, etherification, alkylation, and combinations thereof using fluorine-containing and non-fluorine-containing reactants to provide the precursor compounds, which, in turn, were caused to react together to yield the fluorine-containing liquid crystal compounds of this invention.

Compounds prepared in the various examples of this invention were characterized by their melting or boiling point, and structures were confirmed by using at least one of the following methods of analysis: chromatography; $^{13}$C—, $^{1}$H—, and $^{19}$F-NMR; and infrared and mass spectroscopies.

The 5-alkyl-2-(4-hydroxyphenyl)pyrimidines used in the examples were prepared using the method described by Zaschke, H. and Stolle, R. in "Synthese niedrigschmelzender Kristallin-Flüssiger Hetercyclen; 5-n-Alkyl-2-[4-n-alkanoyloxy-phenyl]pyrimidine", Z. Chem. 15, 441–43 (1975).

EXAMPLES

Examples 1–14 describe procedures for preparing the intermediate compounds of this invention which are useful in preparing the liquid crystal compounds of the invention.

Example 1

Preparation of 2,2,3,3,4,4-Hexafluoro-5-methoxypentyl Trifluoromethanesulfonate 60 g potassium hydroxide (0.9430 moles) and 400 ml absolute ethanol were placed in a 3 neck 1-liter flask fitted with a mechanical stirrer, reflux condenser, and a septum. The resulting mixture was stirred until all of the KOH was dissolved. 100 g (0.4715 moles) of 2,2,3,3,4,4-hexafluoropentane-1,5-diol [prepared essentially as described by I.L. Knunyants, L. Chih-yan and V. V. Shokina, Advances in Chem. (Uspekhi Khimi) 32, Original 1502, Eng. Trans. 461–76 (1963); Translation RSIC-165 (Redstone Information Center)] was added, and the mixture was stirred again until it became a homogeneous liquid. Then, with continued stirring, 1 g of potassium iodide was added, and the mixture was heated to reflux. Finally, 17.6 ml of methyl iodide (0.2829 moles) was added via syringe over a 10 minute period. A precipitate formed during the methyl iodide addition. The mixture was held at reflux for 30 minutes after the addition was complete, and then was cooled to room temperature. The resulting mixture was diluted with water to a volume of 2 liters and was made acidic with concentrated HCl. The diluted, acidified mixture was placed in a separatory funnel, and the product was extracted from the aqueous solution with diethyl ether by washing with two 400 ml ether aliquots followed by two 200 ml ether aliquots. The resulting ether layers were then combined, and the ether was stripped using a rotary evaporator. The residue was purified using flash chromatography on 600 g of silica gel, eluting 2,2,3,3,4,4-hexafluoro-5-methoxypentanol, the desired alcohol, with a 95/5 blend of chloroform/acetonitrile, and then the remaining diol was recovered by eluting with an 85/15 chloroform/acetonitrile blend. The yield of 2,2,3,3,4,4-hexafluoro-5-methoxypentanol was 27.4 g (43% yield), with 61 g of unreacted diol starting material recovered.

23.4 g of 5-methoxy-2,2,3,3,4,4-hexafluoropentanol made as described above was dissolved in 23 ml of methylene chloride. The resulting methylene chloride solution was placed in a flask fitted with a magnetic stirrer, thermometer, and addition funnel. Triethylamine (11.4 g) was added to the flask, and the internal temperature rose to 40° C. The flask was cooled to 5° C. in an ice bath, and then trifluoromethanesulfonic anhydride (36.8 g) was added slowly with mixing so that the temperature did not exceed 10° C. The reaction mixture was allowed to stir overnight with warming to room temperature. Water (25 ml) and methylene chloride (15 ml) were added, then the mixture was shaken and was allowed to phase split. The resulting lower product phase was then washed with 50 ml of 3.5% aqueous HCl, followed by 20 ml of water. The methylene chloride phase was then stripped off at atmospheric pressure. The product cut distilled at a head temperature of 80°–85° C. at 5.5 mm Hg (5.5 torr). A total of 30.3 g of product was obtained. Fluorine nmr showed this material to consist of the following composition (mole %): 88% $CH_3OCH_2(CF_2)_3CH_2OSO_2CF_3$, 1% $CF_3SO_2OCF_3$, 2% $(CF_3SO_2OCF_2)_2CF_2$, 5% $CF_3SO_2N(CH_2CH_3)_2$, and 3% $CH_3OCH_2CF_2CF_2-R_f$, where $R_f$ is a short perfluorinated alkyl chain.

F-nmr (CFCl$_3$, CFCl$_3$ internal standard): $CH_3OCH_2CF_2(A)$ $CF_2(B)$ $CF_2(C)$ $CH_2OSO_2CF_3(D)$, A −121.0 (pentet), B −126.6 (singlet), C −120.1 (multiplet), D −75.1.

Proton-nmr (CFCl$_3$, TMS internal standard, ): $CH_3(1)OCH_2(2)CF_2CF_2CF_2CH_2(3)OSO_2CF_3$, 1 3.45 ppm (triplet, J=0.6 Hz), 2 3.83 ppm (triplet of triplets, J$_1$=13.8 Hz, J$_2$=3.1 Hz), 3 4.81 ppm (triplet, J=13.1 Hz).

Example 2

Preparation of 2,2,3,3,4,4-Hexafluoro-5-butoxypentyl Trifluoromethanesulfonate 60 g potassium hydroxide (0.9430 moles) and 400 ml absolute ethanol were placed in a 3 neck 1-liter flask fitted with a mechanical stirrer, a reflux condenser, and a septum. The resulting mixture was stirred until all of the KOH was dissolved. Then 100 g (0.4715 moles) of 2,2,3,3,4,4-hexafluoropentane-1,5-diol (prepared essentially as described supra) was added, and the mixture was again stirred until it became homogeneous. When homogeneous, stirring was continued, 1 g of potassium iodide was added, and the mixture was heated to reflux. Finally, 32 ml (0.2829 moles) of iodobutane was added via syringe over a 15 minute period. A precipitate formed during the iodobutane addition. The mixture was held at reflux for 1.5 hours after the addition was complete, and then was cooled to room temperature. The resulting mixture was diluted to a volume of 800 ml with water, was made acidic with concentrated HCl, and finally was diluted to a volume of 1.5 liters with additional water. The diluted, acidified mixture was placed in a separatory funnel, and the products were extracted from the aqueous solution by washing three times with 200 ml aliquots of diethyl ether. The resulting ether layers were then combined, and the ether was stripped using a rotary evaporator. The residue was purified using flash chromatography on 600 g of silica gel, eluting 2,2,3,3,4,4-hexafluoro-5-butoxypentanol, the desired alcohol, with a 95/5 chloroform/acetonitrile blend to give a 25.8 g of product.

88 g of 2,2,3,3,4,4-hexafluoro-5-butoxypentanol (made as described above) and 47.9 g of triethylamine were mixed together in a flask fitted with a dry ice (−78° C.) finger condenser, thermometer, dip tube for gas addition, and an overhead stirrer. The system was purged with dry nitrogen and was kept under slightly positive nitrogen pressure. With good stirring, the flask was cooled with dry ice to an internal temperature of −14° C. At this time, the nitrogen was shut off and addition of 81 g of 99% pure trifluoromethanesulfonyl fluoride gas was begun. The reaction was allowed to run for two hours to give 145 g of crude product. The crude product was washed with 90 ml of deionized water, followed by 90 ml of 3.5% aqueous HCl and 90 ml of water. The washed product was distilled at a head temperature of 91°–95° C. to give 114 g (87% yield) of 2,2,3,3,4,4-hexafluoro-5-butoxypentyl trifluoromethanesulfonate.

Example 3

Preparation of 2,2,3,3,4,4-Hexafluoro-5-ethoxypentyl Trifluoromethanesulfonate 30.8 g potassium hydroxide was dissolved in 400 ml of water, 100 g (0.4715 moles) of 2,2,3,3,4,4-hexafluoropentane-1,5-diol (prepared essentially as described supra) was added, and the resulting mixture was heated to 90° C. Over a period of one hour, 74.9 g (0.480 moles) of ethyl iodide was added to the flask via an addition funnel with rapid stirring. The reaction flask was then heated to reflux for two hours. The reaction mixture was cooled to room temperature, and the bottom product phase (87.1 g) was split away from the aqueous layer. The crude product was distilled at 6.0 mm Hg (6.0 torr) to give 58.8 g of 2,2,3,3,4,4-hexafluoro-5-ethoxypentanol distilling at 85°–91° C. (conversion=68%; yield based on converted material=76%).

50 g of the 2,2,3,3,4,4-hexafluoro-5-ethoxypentanol prepared above was dissolved in 50 g of methylene chloride. The resulting solution was placed in a flask fitted with a magnetic stirrer, thermometer, and addition funnel. 22 g of triethylamine was added to the flask, causing a rise in internal temperature to 40° C. The flask was cooled to 5° C. in an ice bath, and then 61.5 g of trifluoromethanesulfonic anhydride was added slowly so that the temperature did not exceed 10° C. The reaction mixture was allowed to stir overnight with warming to room temperature. 50 ml of water and 25 ml of methylene chloride were added, then the mixture was mixed and allowed to phase split. The resulting lower product phase was then washed sequentially with 50 ml of 3.5% aqueous hydrochloric acid and 20 ml of deionized water. The methylene chloride was then stripped off at atmospheric pressure. The residue was distilled at a head temperature of 69°–74° C. at 1.5 mm Hg (1.5 torr) pressure. A total of 62 g of 2,2,3,3,4,4-hexafluoro-5-ethoxypentyl trifluoromethanesulfonate was obtained.

Example 4

Preparation of 4-(5-Ethoxy-2,2,3,3,4,4-hexafluoropentoxy)phenol 2.8 g of 60% sodium hydride in mineral oil was added to 100 ml of dry 1,2-dimethoxyethane. The mixture was stirred, and 10 g (0.0499 moles) of 4-benzyloxyphenol was added. The resulting solution was stirred for 30 minutes more, then was cooled down to room temperature using an ice bath. 19 g (0.0511 moles) of 5-ethoxy-2,2,3,3,4,4-hexafluoropentyl trifluoromethanesulfonate (prepared essentially as in Example 3) was then added slowly. When the triflate addition was complete, the ice bath was removed, and the product-containing mixture was stirred at room temperature overnight. The solvent was then removed under reduced pressure, and 200 ml of water, followed by 150 ml of diethyl ether, were added sequentially with stirring. Once all of the solids had dissolved, two homogeneous liquid layers formed. The layers were separated, and the aqueous layer was extracted twice with 150 ml aliquots of diethyl ether. The resulting ether layers were then combined, were washed once with 125 ml of 1 N aqueous sodium hydroxide and twice with 150 ml aliquots of deionized water, were dried using anhydrous magnesium sulfate, and were stripped to dryness using a rotary evaporator. The resulting solid was dissolved in ethanol and was hydrogenated for 18 hours at 60 psi (3100 torr) in the presence of a 10%-palladium-on-carbon catalyst. When the hydrogenation was complete, the catalyst solid was removed by filtration, and the solvent from the filtrate was removed using a rotary evaporator. The resulting material was purified using chromatography on silica gel (2.5% methanol in chloroform) to yield 2.85 g of 4-(5-ethoxy-2,2,3,3,4,4-hexafluoropentoxy)phenol.

Example 5

Preparation of 4-(5-Butoxy-2,2,3,3,4,4-hexafluoropentoxy)phenol

In this example, a compound was prepared in essentially the same manner as that described in Example 4, except that 5-butoxy-2,2,3,3,4,4-hexafluoropentyl trifluoromethanesulfonate (19.6 g, 0.049 moles) was substituted for the 5-ethoxy-2,2,3,3,4,4-hexafluoropentyl trifluoromethanesulfonate. In this case, 6.13 g of 4-(5-butoxy-2,2,3,3,4,4-hexafluoropentoxy)phenol product resulted.

Example 6

Preparation of 4'-(5-Butoxy-2,2,3,3,4,4-hexafluoropentoxy)-4-hydroxybiphenyl

Sodium hydride (0.3 g, 60% in mineral oil) was added to a solution of 4-4'-biphenol (4.6 g, 25 mmol) in N,N-dimethylformamide (100 ml). The solution was stirred under a nitrogen atmosphere for 0.5 hours and then heated to 60° C. 2,2,3,3,4,4-hexafluoro-5-butoxypentoxytriflate (5.0 g, 12.5 mmol) (from example 2) was then added by syringe to the solution. The reaction mixture was stirred for 2 hours at 70° C. and then cooled to room temperature. The solution was quenched with 100 ml of H20 and extracted with three 100 ml aliquots of diethyl ether. The organic extracts were collected, dried using MgSO4, filtered and concentrated. The product was then purified by flash chromatography to give 3.06 g (55% yield) of the product as a white solid (mg =87°–90° C).

Example 7

Preparation of 6-(5-Ethoxy-2,2,3,3,4,4-hexafluoropentoxy)-2-hydroxynapthalene 0.7 g of 60% sodium hydride in mineral oil was added to 25 ml of dry 1,2-dimethoxyethane. The contents were stirred, and 2.5 g (0.010 moles) of 6-benzyloxy-2napthol was slowly added. After stirring the resulting solution for 20 minutes at room temperature, it was cooled with an ice bath. 4.1 g (0.011 moles) of 5-ethoxy-2,2,3,3,4,4-hexafluoropentyl trifluoromethanesulfonate (prepared essentially as in Example 3) was then added slowly. When this addition was complete, the ice bath was removed, and the product-containing mixture was stirred overnight at room temperature. The solvent was then removed under reduced pressure, and 30 ml of water, followed by 30 ml of diethyl ether, were added sequentially. Once all of the solids had dissolved, two homogeneous liquid layers formed. The layers were separated, and the aqueous layer was extracted twice with 25 ml aliquots of diethyl ether. The resulting ether layers were combined, washed three times with 20 ml aliquots of deionized water, dried with anhydrous magnesium sulfate, and stripped to dryness using a rotary evaporator. The resulting solid was dissolved in tetrahydrofuran and was hydrogenated at 60 psi in the presence of catalytic 10% palladium on carbon for 18 hours. When the hydrogenation was complete, the catalyst was removed by filtration, and the solvent was removed on a rotary evaporator. The resulting brown semisolid material was then purified by using chromatography on silica gel (2.5% methanol in chloroform) to yield 1.64 g of 6-(5-ethoxy-2,2,3,3,4,4-hexafluoropentoxy)-2-hydroxynapthalene product.

Example 8

Preparation of 6-(5-Butoxy-2,2,3,3,4,4-hexafluoropentoxy)-2-hydroxynapthalene

In this example, a compound was prepared in essentially the same manner as that described in Example 7, except that 4.0 g (0.010 moles) of 5-butoxy-2,2,3,3,4,4-hexafluoropentyl trifluoromethanesulfonate (prepared essentially as in Example 2) was substituted for the 5-ethoxy-2,2,3,3,4,4-hexafluoropentyl trifluoromethanesulfonate to provide 2.82 g of 6-(5-butoxy-2,2,3,3,4,4-hexafluoropentoxy)-2-hydroxynapthalene product.

Example 9

Preparation of 4-(5-Butoxy-2,2,3,3,4,4-hexafluoropentoxy)benzoic acid 0.6 g of 60% sodium hydride in mineral oil was added to 5 ml of N,N-dimethylformamide in a three-necked flask under an inert atmosphere. 1.96 g (0.0129 moles) of methyl hydroxybenzoate was dissolved separately in a mixture of 10 ml of toluene and 5 ml of dimethylformamide. The methyl hydroxybenzoate solution was then added to the sodium hydride suspension over a period of 15 minutes. The reaction was allowed to stir at room temperature for one hour. 5.2 g (0.0129 moles) of 5-butoxy-2,2,3,3,4,4-hexafluoropentyl trifluoromethanesulfonate (prepared essentially as in Example 2) was then added and the flask was heated to 116° C. for one hour. The reaction mixture was cooled to room temperature and was poured into 25 ml of water. Once all of the solids had dissolved, two homogeneous layers formed. The upper crude product phase was split off and was re-washed with an additional 25 ml of water. The purified organic product phase was then stripped at 0.2 mm Hg (0.2 torr) until the pot temperature reached 120° C. The desired intermediate, methyl 4-(5-butoxy-2,2,3,3,4,4-hexafluoropentoxy)benzoate, was then distilled at 0.03 mm Hg (0.03 torr) and at 170°–172° C. head temperature.

Subsequently, the methyl 4-(5-butoxy-2,2,3,3,4,4-hexafluoropentoxy)benzoate was heated at reflux with 20 ml of 10% aqueous KOH for 2 hours. The resulting hydrolyzed carboxylate salt reaction product mixture was then cooled to room temperature and was acidified with concentrated (98%) sulfuric acid. The desired fluorinated benzoic acid precipitate was filtered from the aqueous solution and was washed twice with 10 ml aliquots of deionized water. The product was dried in a vacuum oven at 60° C. and a pressure of 0.2 mm Hg (0.2 torr). A total of 9.5 g of the desired 4-(5-butoxy-2,2,3,3,4,4-hexafluoropentoxy)benzoic acid was recovered.

Example 10

Preparation of 6-Ethoxy-2,2,3,3,4,4,5,5-octafluorohexyl Trifluoromethanesulfonate 15.4 g potassium hydroxide was dissolved in 200 ml of deionized water, 62 g of 2,2,3,3,4,4,5,5-octafluorohexane-1,6-diol [prepared essentially as described by I.L. Knunyants, L. Chih-yan and V. V. Shokina, Advances in Chem. (Uspekhi Khimi) 32, Original 1502, Eng. Trans. 461–476 (1963); Translation RSIC-165 (Redstone Information Center)] was added, and the mixture was heated to 90° C. Over a period of one hour, 35.7 g of ethyl iodide was added with rapid stirring to the flask via an addition funnel. The reaction mixture was then heated to reflux for two hours. The reaction mixture was cooled to room temperature, and the bottom product phase (54 g crude product) was split away from the aqueous layer. The crude product was distilled at 92°–100° C. at 5.5 mm Hg (5.5 torr) to give 29.1 g of 6-ethoxy-2,2,3,3,4,4,5,5-octafluorohexanol.

20 g of the 6-ethoxy-2,2,3,3,4,4,5,5-octafluorohexanol made above was dissolved in 20 g of methylene chloride. The resulting solution was placed in a flask fitted with a magnetic stirrer, thermomether, and addition funnel. 7.3 g of triethylamine was added to the flask, causing the temperature of the mixture to rise to 40° C. The flask was cooled to 5° C. in an ice bath, and then 61.5 g of trifluoromethanesulfonic anhydride was added slowly so that the temperature of the contents did not exceed 10° C. The reaction mixture was allowed to stir overnight with warming to room temperature. 20 ml of deionized water and 20 ml of methylene chloride were added, then the mixture was mixed and allowed to phase split. The resulting lower product phase was then washed sequentially with 20 ml of 3% aqueous HCl and 20 ml of deionized water. The methylene chloride was then stripped off at atmospheric pressure. The product residue was distilled at a head temperature range of 87-90° C. at 2.5 mm Hg (2.5 torr) pressure. A total of 20.1 g of 6-ethoxy-2,2,3,3,4,4,5,5-octafluorohexyl trifluoromethanesulfonate was obtained.

Example 11

Preparation of 4'-(5-Ethoxy-2,2,3,3,4,4-hexafluoropentoxy)-4-hydroxybiphenyl

This compound was prepared from 4-4'-biphenol and 2,2,3,3,4,4,-hexafluoro-5-ethoxypentoxytrifluoromethanesulfonate (prepared essentially as in Example 3) essentially as described in Example 6.

Example 12

Preparation of 4-Hydroxyphenyl-(4-(5-butoxy-2,2,3,3,4,4-hexafluoropentoxy)) benzoate 11.3 ml of oxalyl chloride solution (2M in methylene chloride) was added to a solution of 8.0 g (0,021 moles) of 4-(5-butoxy-2,2,3,3,4,4-hexafluoropentoxy)benzoic acid (prepared essentially as in Example 9) in 16 ml of methylene chloride. A small drop of N,N-dimethylformamide was added, and the solution was stirred under a nitrogen atmosphere at room temperature for 1 hour. The solution was then concentrated by evaporation to remove excess oxalyl chloride from the solution. The resulting acid chloride was redissolved in 20 ml of methylene chloride, and this solution was added to a solution of 4.1 g (0.21 moles) monobenzylhydroquinone, 2.5 ml pyridine, and 20 ml methylene chloride. The reaction mixture was stirred at room temperature overnight. 5 g of silica gel was then added to the flask, and the solvent was removed under reduced pressure. The product was isolated by chromatography to obtain 5.56 g of a white solid. The desired product was obtained by hydrogenation of the white solid at 60 psi (3100 torr) pressure using 10% palladium on carbon in tetrahydrofuran. The reaction mixture was then filtered through celite and concentrated to obtain 5.1 g of 4-hydroxyphenyl-(4-(5-butoxy-2,2,3,3,4,4-hexafluoropentoxy) benzoate, a white solid.

Example 13

Preparation of 5-(5-Butoxy-2,2,3,3,4,4-hexafluoropentoxy)-2-(4-hydroxyphenyl)pyrimidine.

In a one-liter flask, 30 g (0.09 moles) of 2benzyloxy-trimethinium perchlorate (prepared essentially according to the procedure of A. Holy and Z. Arnold, Collection Czechoslov. Chem. Commun. 38, 1372 (1973)), 15.6 g (0.09 moles) of p-hydroxybenzamidine hydrochloride, 82.5 ml (0.36 moles) of 25% sodium methoxide in methanol, and 500 ml of ethanol were combined. The resulting mixture was heated to reflux overnight, and then cooled to room temperature. Then, 75 ml of glacial acetic acid and 300 ml of deionized water was added to the flask, resulting in precipitation of the product. The product was collected by filtration, washed with water, and air dried. The yield of 5-benzyloxy-2-(4-hydroxyphenyl)pyrimidine was 23.06 g (92%). This material was then hydrogenated on a Parr Hydrogenator with catalytic 10% palladium on carbon in tetrahydrofuran under 413.7 kPa hydrogen pressure for about 18 hours. When the hydrogenation was complete, the catalyst was removed by filtration, and the solvent was removed on a rotary evaporator to yield 5-hydroxy-2-(4-hydroxyphenyl)pyrimidine. The final product, 5-(5-butoxy-2,2,3,3,4,4-hexafluoropentoxy)-2-(4hydroxyphenyl)-pyrimidine, was prepared from 5-hydroxy-2-(4-hydroxyphenyl)pyrimidine and 5-butoxy-2,2,3,3,4,4hexafluoropentyltrifluoromethanesulfonate (prepared essentially as in Example 2) essentially as described in Example 6.

Example 14

Preparation of Ethoxy-(1,1,1',1'-tetrahydroperfluoro(-tetraethylene glycol)) Nonafluorobutanesulfonate Methyl perfluoro-oxydi(ethoxyacetate), prepared by fluorination of tetraethylene glycol diacetate, and subsequent methanolysis, was reduced to 1,1,1', 1'-tetrahydroperfluorotetraethylene glycol by sodium borohydride reduction. 19.7 g of the resulting 1,1,1',1'-tetrahydroperfluoro(tetraethylene glycol) was mixed with 3.8 g of sodium hydroxide, 10 ml of deionized water, and 0.8 g of tetrabutylammonium hydrogen sulfate, and was heated to 63° C. Then, 7.5 g of ethyl iodide was slowly added over a period of 1.5 hours, and after the addition the reaction mixture was heated to 65°-70° C., which caused the mixture to split into two phases. The resulting lower phase was sampled and was found by gas chromatography ($\frac{1}{8}$" diameter, 12 ft 3% OV-121, 50°-250° C., one min post injection interval, 20 deg/min) to be 23% unreacted $HOCH_2CF_2O(CF_2CF_2O)_2CF_2CH_2OH$ (8.77 min), 41% $C_2H_5OCH_2CF_2O(CF_2CF_2O)_2CF_2CH_2OH$ (8.91 rain), and 24% $C_2H_5OCH_2CF_2O(CF_2CF_2O)_2CF_2CH_2OC_2H_5$ (9.21 min). The gc/mass spectrum confirmed the identity of these peaks. 100 ml of deionized water was added to the reaction mixture, and it was stirred at room temperature for 5 minutes. The lower phase (18.7 g) was split off and then washed with 6.4 g of KOH dissolved in 200 ml of deionized water. The crude product (15.6 g) was shown by gc to be 63% $C_2H_5OCH_2CF_2O(CF_2CF_2O)_2CF_2CH_2OH$ (8.91 min) and 26% $C_2H_5OCH_2CF_2O(CF_2CF_2O)_2CF_2CH_2OC_2H_5$ (9.21 min). The crude product was distilled at 0.3 mm Hg (0.3 torr) to give 8.5 g material which came over in the 66°-74° C. range. The distilled material was shown by gc to be 77% desired product, $C_2H_5OCH_2CF_2O(CF_2CF_2O)_2CF_2CH_2OH$ (8.91 min), and 22% $C_2H_5OCH_2CF_2O$ $(CF_2CF_2O)_2CF_2CH_2OC_2H_5$ (9-21 min). Infrared analysis showed a spectrum consistent with the desired product.

8.5 g of $C_2H_5OCH_2CF_2O(CF_2CF_2O)_2CF_2CH_2OH$ (made as described above) was dissolved in 2.2 g of triethylamine and was placed in a flask with an overhead stirrer, thermometer and addition funnel. Under a stream of dry nitrogen the flask was cooled to -10° C. using a bath of water/methanol/dry ice. Over a period of one minute 6.4 g of $C_4F_9SO_2F$ (made essentially as described by T. Abe and S. Nagase, "Electrochemical Fluorination (Simons Process) as a Route to Perfluorinated Organic Compounds of Industrial Interest," *Preparation, Properties and Industrial Applications of Organofluorine Compounds*, 37–38 (1982)) was added to the rapidly stirred flask contents. After this sulfonyl fluoride addition, the batch was allowed to warm up to 0° C. and was stirred for an additional 1.5 hours. Ten minutes after the onset of stirring, the clear yellow solution began to cloud up from the formation of triethylammonium fluoride. After two more hours, 20 g of deionized water was added with good stirring. The yellow fluorochemical phase was split away from the aqueous phase to give 13.1 g of crude product. This crude product was then washed with 20 g of 3.5% aqueous HCl, followed by 20 g of water, and 10.8 g of fluorochemical product was obtained. The crude product was distilled at 0.01 mm Hg (0.01 torr) at a head temperature of 80°-96° C. to give 7.8 g of material which was 77% ethoxy-(1,1,1',1'-tetrahydroperfluoro(tetraethylene glycol)) nonafluorobutanesulfonate (by gc). Infrared spectroscopy and gc/ms was consistent with the desired structure.

Examples 15–44 describe procedures for preparing the liquid crystal compounds of this invention. The chemical structure of each compound is given in Table 1.

Example 15

Preparation of 5-Octyl-2-(4'-(5-ethoxy-2,2,3,3,4,4-hexafluoropentoxy)biphenyl)pyrimidine (Compound 1, Table 1)

4-cyano-4'-hydroxybiphenyl was converted to the corresponding amidine hydrochloride via the method of M.W. Partridge and W.F. Short, J. Chem. Soc., 390 (1947). The resulting amidine hydrochloride (10 g, 0.0402 moles) and 2-octyl-3-dimethylaminoacrolein (8.5 g, 0.0402 moles, prepared essentially as described by Z. Arnold and F. Sorm, Coll. Czech. Chem. Commun., 23, 452 (1958)) were then treated with 37 ml of 25% sodium methoxide in methanol (0.1608 moles) in 150 ml of absolute ethanol. The resulting mixture was heated to reflux overnight. After cooling to room temperature, the solvent was removed under reduced pressure. 100 ml of water, 100 ml of diethyl ether, and 10 ml of glacial acetic acid were then added to the flask, and the mixture was stirred until all of the solids dissolved. The resulting two homogeneous layers were separated in a separatory funnel. The aqueous layer was extracted twice with 50 ml aliquots of diethyl ether. The three ether layers were combined, were washed three times with 50 ml aliquots of water, and were dried with anhydrous magnesium sulfate. Finally, the solvent was removed under reduced pressure, and the resulting solid was recrystallized from hot acetonitrile to give 5.38 g of 5-octyl-2-(4'-hydroxybiphenyl) pyrimidine (37% yield).

A 50 ml flask was charged with 0.2 g (0.004 moles) of 60% sodium hydride in mineral oil, 10 ml of toluene, 10 ml of N,N-dimethylformamide, and 1 g (0.00277 moles) of 5-octyl-2-(4'-hydroxybiphenyl) pyrimidine (made as described above) under an atmosphere of dry nitrogen. The mixture was stirred at room temperature for 1.5 hours. 1.03 g (0.00277 moles) of 2,2,3,3,4,4-hexafluoro-5-ethoxypentyl trifluoromethanesulfonate (prepared essentially as in Example 3) was then added, and the resulting mixture was heated to 100° C. for 1.5 hours. After cooling to room temperature, the contents of the flask were poured into a separatory funnel containing 60 ml of water and 20 ml of toluene. After mixing, the resulting layers were separated, and the aqueous layer was extracted twice with 20 ml aliquots of toluene. The three organic layers were combined, washed three times with 30 ml aliquots of of deionized water, dried with anhydrous sodium sulfate, and filtered. The solvent from the filtrate was removed under reduced pressure. The resulting material was purified by flash chromatography on silica gel (chloroform) to yield 0.41 g of white solid, 5-octyl-2-(4'-(5-ethoxy-2,2,3,3,4,4-hexafluoropentoxy)biphenyl)pyrimidine.

Example 16

Preparation of 5-Octyl-2-(4'-(5-butoxy-2,2,3,3,4,4hexafluoropentoxy)biphenyl)pyrimidine (Compound 2, Table 1)

5-octyl-2-(4'-(5-butoxy-2,2,3,3,4,4-hexafluoropentoxy)biphenyl)pyrimidine was prepared by essentially the method of Example 15, except that 2,2,3,3,4,4-hexafluoro-5-butoxypentyl trifluoromethanesulfonate (prepared essentially as in Example 2) was used in place of 5-ethoxy-2,2,3,3,4,4-hexafluoropentyl trifluoromethanesulfonate, to yield 0.24 g of 5-octyl-2-(4'-(5-butoxy-2,2,3,3,4,4-hexafluoropentoxy)biphenyl)pyrimidine.

Example 17

Preparation of 4-(5-Butoxy-2,2,3,3,4,4-hexafluoropentoxy)phenyl 4-Decyloxybenzoate (Compound 3, Table 1)

0.45 g (0.0016 moles) of 4-decyloxybenzoic acid and 0.58 g (0.0016 moles) of 4-(5-butoxy-2,2,3,3,4,4-hexafluoropentoxy)phenol (prepared essentially as in Example 5) were dissolved in 25 ml of methylene chloride. N,N-dicyclohexylcarbodiimide (0.35 g, 0.0017 moles) was added to the reaction mixture, followed by 0.05 g of 4-(N,N-dimethylamino)pyridine. The resultant mixture was stirred at room temperature under nitrogen for 18 hours. The resulting urea precipitate was removed from the product solution by filtration, and the filtrate was concentrated on a rotary evaporator at reduced pressure. The crude product was purified by flash chromatography on silica gel (chloroform) to yield 0.12 g of 4-(5-butoxy-2,2,3,3,4,4-hexafluoropentoxy)phenyl 4-decyloxybenzoate.

Examples 18–25

In Examples 18–25, Compounds 4–11 of Table 1 were prepared essentially as in Example 17, except that the precursor compounds indicated below were substituted for the 4-decyloxybenzoic acid and the 4-(5-butoxy-2,2,3,3,4,4-hexafluoropentoxy)phenol in the esterification reaction.

Example 18

Preparation of 4-Octyloxyphenyl 4-(5-Butoxy-2,2,3,3,4,4-hexafluoropentoxy)benzoate (Compound 4, Table 1)

4-Octyloxyphenyl 4-(5-butoxy-2,2,3,3,4,4-hexafluoropentoxy)benzoate (Compound 4, Table 1) was prepared by esterification of 4-(5-butoxy-2,2,3,3,4,4-hexafluoropentoxy)benzoic acid (prepared essentially as in Example 9) with 4-octyloxyphenol.

Example 19

Preparation of 4-(5-Ethoxy-2,2,3,3,4,4hexafluoropentoxy)phenyl 3-Chloro-4-octyloxybenzoate (Compound 5, Table 1)

4-(5-Ethoxy-2,2,3,3,4,4-hexafluoropentoxy)phenyl 3-chloro-4-octyloxybenzoate (Compound 5, Table 1) was prepared by esterification of 4-(5-ethoxy-2,2,3,3,4,4-hexafluoropentoxy)phenol (prepared essentially as in Example 4) with 3-chloro-4-octyloxybenzoic acid.

Example 20

Preparation of 4-(5-Ethoxy-2,2,3,3,4,4-hexafluoropentoxy)phenyl 6-(4-Methylhexyloxy)nicotinate (Compound 6, Table 1)

4-(5-Ethoxy-2,2,3,3,4,4-hexafluoropentoxy)phenyl 6-(4-methylhexyloxy)nicotinate (Compound 6, Table 1) was prepared by esterification of 4-(5-ethoxy-2,2,3,3,4,4-hexafluoropentoxy)phenol (prepared essentially as in Example 4) with 6-(4-methylhexyloxy)nicotinic acid.

Example 21

Preparation of 4-(5-Butoxy-2,2,3,3,4,4-hexafluoropentoxy)phenyl 6-(4-Methylhexyloxy)nicotinate (Compound ?, Table 1)

4-(5-Butoxy-2,2,3,3,4,4-hexafluoropentoxy)phenyl 6-(4-methylhexyloxy)nicotinate (Compound 7, Table 1) was prepared by esterification of 4-(5-butoxy-2,2,3,3,4,4-hexafluoropentoxy)phenol (prepared essentially as in Example 5) with 6-(4-methylhexyloxy)nicotinic acid.

Example 22

Preparation of 6-(5-Butoxy-2,2,3,3,4,4-hexafluoropentoxy)-2-hydroxynapthalene Octyloxybenzoate (Compound 8, Table 1)

6-(5-Butoxy-2,2,3,3,4,4-hexafluoropentoxy)-2-hydroxynapthalene octyloxybenzoate (Compound 8, Table 1) was prepared by esterification of 6-(5-butoxy-2,2,3,3,4,4-hexafluoropentoxy)-2-hydroxynapthalene (prepared essentially as in Example 8) with octyloxybenzoic acid.

Example 23

Preparation of 6-(5-Ethoxy-2,2,3,3,4,4-hexafluoropentoxy)-2-hydroxynapthalene Decyloxybenzoate (Compound 9, Table 1)

6-(5-Ethoxy-2,2,3,3,4,4-hexafluoropentoxy)-2-hydroxynapthalene decyloxybenzoate (Compound 9, Table 1) was prepared by esterification of 6-(5-ethoxy-2,2,3,3,4,4-hexafluoropentoxy)-2-hydroxynapthalene (prepared essentially as in Example 7) with decyloxybenzoic acid.

Example 24

Preparation of 4,-(5-Ethoxy-2,2,3,3,4,4-hexafluoropentoxy)-4-hydroxybiphenyl Octyloxybenzoate (Compound 10, Table 1)

4,-(5-Ethoxy-2,2,3,3,4,4-hexafluoropentoxy)-4-hydroxybiphenyl octyloxybenzoate (Compound 10, Table 1) was prepared by esterification of 4'-(5-ethoxy- 2,2,3,3,4,4-hexafluoropentoxy)-4-hydroxybiphenyl (prepared essentially as in Example 6) with octyloxybenzoic acid.

Example 25

Preparation of Hydroquinone-mono-trans-4-pentylcyclohexanecarboxylate 4-(5-Butoxy-2,2,3,3,4,4-hexafluoropentoxy)benzoate (Compound 11, Table 1)

Hydroquinone-mono-trans-4-pentylcyclohexanecarboxylate 4-(5-butoxy-2,2,3,3,4,4-hexafluoropentoxy)benzoate (Compound 11, Table 1) was prepared by esterification of 4- (5-butoxy-2,2,3,3,4,4-hexafluoropentoxy)benzoic acid (prepared essentially as in Example 9) with hydroquinone-mono-trans-4-pentylcyclohexanecarboxylate.

Example 26

Preparation of 5-Decyl-2-(4-(5-ethoxy-2,2,3,3,4,4-hexafluoropentoxy)phenyl)pyrimidine (Compound 12, Table 1)

0.4 g of sodium hydride (97% pure), 15 ml of toluene and 15 ml of anhydrous N,N-dimethylformamide were placed in a 100 flask fitted with a magnetic stir bar and water-cooled condensor with a dry nitrogen inlet. Then 3.3 g (0.0106 moles) of 5-decyl-2-(4-hydroxyphenyl)pyrimidine was slowly added. After stirring for 30 minutes at room temperature, 3.9 g (0.0106 moles) of 5-ethoxy-2,2,3,3,4,4-hexafluoropentyl trifluoromethanesulfonate (made essentially as in Example 3) was added and the contents stirred overnight at room temperature. The contents then were poured into a separatory funnel containing 30 ml of water. The funnel was shaken and the two layers formed were allowed to separate. The aqueous layer was extracted twice with two 15 ml aliquots of toluene. The organic layers were combined, then washed four times with 20 ml aliquots of deionized water, dried with anhydrous sodium sulphate, and stripped of solvent using a rotary evaporator. The resulting oil was chromatographed on silica gel (chloroform) to obtain 2.07 g of 5-decyl-2-(4-(5-ethoxy-2,2,3,3,4,4-hexafluoropentoxy)phenyl)pyrimidine.

Example 27

Preparation of 5-Decyl-2-(4-ethoxy-(1,1,1', 1'-tetrahydroperfluoro(tetraethylene glycol)oxy)phenyl)pyrimidine (Compound 13, Table 1)

In this example, a compound was prepared in essentially the same manner as that described in Example 26, except that ethoxy-(1,1,1',1'-tetrahydroperfluoro(tetraethylene glycol)) nonafluorobutanesulfonate (prepared essentially as in Example 14) was substituted for the 5-ethoxy-2,2,3,3,4,4-hexafluoropentyl trifluoromethanesulfonate to provide 5-decyl-2-(4-ethoxy-(1,1,1',1'-tetrahydroperfluoro(tetraethylene glycol)oxy)phenyl)pyrimidine, the desired product.

Example 28

Preparation of 5-Decyl-2-(4-(6-ethoxy-2,2,3,3,4,4,5,5-octafluorohexoxy)phenyl)pyrimidine (Compound 14, Table 1)

In this example, a compound was prepared in essentially the same manner as that described in Example 26, except that 4.5 g (0.0106 moles) of 6-ethoxy-2,2,3,3,4,4,5,5-octafluorohexyl trifluoromethanesulfonate (prepared essentially as in Example 10) was substituted for the 6-ethoxy-2,2,3,3,4,4-hexafluoropentyl trifluoromethanesulfonate, to provide 1.67 g of 5-decyl-2-(4-(6-ethoxy-2,2,3,3,4,4,5,5-octaafluorohexoxy)phenyl)pyrimidine.

Example 29

Preparation of 5-Butyl-2-(4-(2,2,3,3,4,4-hexafluoro-5methoxypentoxy)phenyl)pyrimidine (Compound 15, Table 1)

Dry sodium hydride (0.5 g, 0.0206 moles) was weighed into a 100 ml flask in a glove bag under dry nitrogen. The flask was then fitted with a magnetic stir bar and a water-cooled condenser with a nitrogen inlet. 20 ml of toluene and 20 ml of anhydrous N,N-dimethylformamide were added, mixing was started, and then 4 g of 4-butyl-2-(4-hydroxyphenyl)pyrimidine (0.0130 moles) was added slowly to control the rate of hydrogen evolution. After stirring at room temperature for 20 minutes, 4.9 g (0.0137 moles) of 2,2,3,3,4,4-hexafluoro-5-methoxypentyl trifluoromethanesulfonate (prepared essentially as in Example 1) was added, and the contents were heated to reflux for 1 hour. After cooling to room temperature, the contents of the flask were poured into a separatory funnel containing 50 ml of water. The funnel was shaken and the two layers formed were allowed to separate. The aqueous layer was extracted twice with 20 ml aliquots of toluene. The organic layers were combined, then were washed three times with 30 ml aliquots of deionized water, dried with anhydrous sodium sulfate, and stripped of solvent using a rotary evaporator. The resulting oil was chromatographed on silica gel, eluting with chloroform, to yield a pale yellow liquid, 5-butyl-2-(4-(2,2,3,3,4,4-hexafluoro-5-methoxypentoxy)phenyl)pyrimidine.

Example 30

Preparation of 5-Octyl-2-(4-(2,2,3,3,4,4-hexafluoro-5-methoxypentoxy)phenyl)pyrimidine (Compound 16, Table 1)

0.6 g of dry (97%) sodium hydride (0.250 moles), 15 ml of toluene and 15 ml of anhydrous N,N-dimethylformamide were placed in a 100 ml flask fitted with a magnetic stir bar and a water-cooled condenser with a nitrogen inlet. Then 3.96 g of 4-octyl-2-(4-hydroxyphenyl)pyrimidine (0.0139 moles) was added slowly to control the rate of hydrogen evolution. After stirring at room temperature for 20 minutes, 5 g (0.0139 moles) of 2,2,3,3,4,4-hexafluoro-5-methoxypentyl trifluoromethanesulfonate (prepared essentially as described in Example 1) was added, and the contents were heated to reflux for 1 hour. After cooling to room temperature, the contents of the flask were poured into a separatory funnel containing 50 ml of water. The funnel was shaken, and the two layers formed were allowed to separate. The aqueous layer was extracted twice with 25 ml aliquots of toluene. The three organic layers were combined, then washed with four times with 25 ml aliquots of deionized water, dried with anhydrous sodium sulfate, and stripped of solvent using a rotary evaporator. The resulting oil was chromatographed on silica gel, eluting with chloroform, to yield 1.51 g of pale yellow liquid, 5-octyl-2-(4-(2,2,3,3,4,4-hexafluoro-5-methoxypentoxy)phenyl)pyrimidine.

Example 31

Preparation of 5-Decyl-2-(4-(2,2,3,3,4,4-hexafluoro-5-methoxypentoxy)phenyl)pyrimidine (Compound 17, Table 1)

0.6 g of dry (97%) sodium hydride (0.250 moles), 15 ml of toluene and 15 ml of anhydrous N,N-dimethylformamide were placed in a 100 ml flask fitted with a magnetic stir bar and a water-cooled condenser with a nitrogen inlet. Then 4.3 g of 4-decyl-2-(4-hydroxyphenyl)pyrimidine (0.0139 moles) was added slowly to control the rate of hydrogen evolution. After stirring at room temperature for 20 minutes, 5 g (0.0139 moles) of 2,2,3,3,4,4-hexafluoro-5-methoxypentyl trifluoromethanesulfonate (prepared essentially as described in Example 1) was added, and the contents were heated to reflux for 1 hour. Upon cooling to room temperature, the contents of the flask were poured into a separatory funnel containing 50 ml of water. The funnel was shaken and the two layers formed were allowed to separate. The aqueous layer was extracted twice with two 25 ml aliquots of toluene. The three organic layers were then combined, washed four times with 25 ml aliquots of deionized water, dried with anhydrous sodium sulfate, and stripped of solvent on a rotary evaporator. The resulting oil was chromatographed on silica gel, eluting with chloroform, to yield a pale yellow liquid. After standing under vacuum overnight, some crystals were observed in the liquid. Upon cooling below room temperature, the material solidified to an off white-solid. The yield was 2.78 g of 5-decyl-2-(4-(2,2,3,3,4,4-hexafluoro-5-methoxypentoxy)phenyl)-pyrimidine.

Example 32

Preparation of 5-Octyl-2-(4-(2,2,3,3,4,4-hexafluoro-5-butoxypentoxy)-phenyl-pyrimidine (Compound 18, Table 1)

0.6 g of dry (97%) sodium hydride (0.250 moles), 15 ml of toluene and 15 ml of anhydrous N,N-dimethylformamide were placed in a 100 ml flask fitted with a magnetic stir bar and a water-cooled condenser with a nitrogen inlet. Then 3.1 g (0.0110 moles) of 4-octyl-2-(4-hydroxyphenyl)pyrimidine was added slowly to control the rate of hydrogen evolution. After stirring at room temperature for 20 minutes, 4.4 g (0.0110 moles) of 2,2,3,3,4,4-hexafluoro-5-butoxypentyl trifluoromethanesulfonate (prepared essentially as in Example 2) was added, and the contents were heated to reflux for 1 hour. Upon cooling to room temperature, the contents of the flask were poured into a separatory funnel containing 50 ml of water. The funnel was shaken and the two layers formed were allowed to separate. The aqueous layer was extracted twice with two 25 ml aliquots of toluene. The three organic layers were then combined, washed four times with 25 ml aliquots of deionized water, dried with anhydrous sodium sulfate, and stripped of solvent on a rotary evaporator. The resulting oil was chromatographed on 100 g of silica gel, eluting with chloroform, to yield 1.35 g of pale yellow liquid, 5-octyl-2-(4-(2,2,3,3,4,4-hexafluoro-5butoxypentoxy)phenyl)pyrimidine, which solidified in the freezer.

Example 33

Preparation of 5-Decyl-2-(4-(2,2,3,3,4,4-hexafluoro-5-butoxypentoxy)-phenyl-pyrimidine (Compound 19, Table 1)

1.0 g of dry (97%) sodium hydride, 30 ml of toluene and 30 ml of anhydrous N,N-dimethylformamide were placed in a 100 ml flask fitted with a magnetic stir bar and a water-cooled condenser with a nitrogen inlet. Then 7.8 g (0.0249 moles) of 4-decyl-2-(4-hydroxyphenyl)pyrimidine was added slowly to control the rate of hydrogen evolution. After stirring at room temperature for 20 minutes, 5 g (0.0249 moles) of 2,2,3,3,4,4-hexafluoro-5-butoxypentyl trifluoromethanesulfonate (prepared essentially as described in Example 2) was added, and the contents were heated to reflux for 0.5 hr. Upon cooling to room temperature, the contents of the flask were poured into a separatory funnel containing 70 ml of water. The funnel was shaken and the two layers formed were allowed to separate. The aqueous layer was extracted twice with 50 ml aliquots of toluene. The three organic layers were combined, then washed four times with 50 ml aliquots of deionized water, dried with anhydrous sodium sulfate, and stripped of solvent on a rotary evaporator . The resulting oil was chromatographed using 175 g of silica gel, eluting with chloroform, to yield 9.32 g of pale yellow liquid, 5-decyl-2-(4-(2,2,3,3,4,4-hexafluoro- 5-butoxypentoxy)-phenyl-pyrimidine.

Example 34

Preparation of 5-Butyl-2-(4-(2,2,3,3,4,4-hexafluoro-5-butoxypentoxy)phenyl)pyrimidine (Compound 20, Table 1)

Dry sodium hydride (0.5 g, 0.0206 moles) was weighed into a 100 ml flask in a glove bag under dry nitrogen. The flask was then fitted with a magnetic stir bar and a water-cooled condenser with a nitrogen inlet. 15 ml of toluene and 15 ml of anhydrous N,N-dimethylformamide were added, and then 2.5 g (0.0110 moles) of 4-butyl-2-(4-hydroxyphenyl)pyrimidine was added slowly to control the rate of hydrogen evolution. After stirring at room temperature for 20 minutes, 4.4 g (0.0110 moles) of 2,2,3,3,4,4-hexafluoro-5-butoxypentyl trifluoromethanesulfonate (prepared essentially as described in Example 2) was added, and the contents were heated to reflux for 1 hour. Upon cooling to room temperature, the contents of the flask were poured into a separatory funnel containing 50 ml of water. The funnel was shaken and the two layers formed were allowed to separate. The aqueous layer was extracted twice with 20 ml aliquots of toluene. The three organic layers were combined, then washed four times with 25 ml aliquots of deionized water, dried with anhydrous sodium sulfate, and stripped of solvent on a rotary evaporator. The resulting oil was chromatographed on silica gel, eluting with chloroform, to yield 2.85 g of pale yellow liquid, 5-butyl-2-(4-(2,2,3,3,4,4-hexafluoro-5-butoxypentoxy)-phenyl)pyrimidine.

Example 35

Preparation of 4-(5-Ethoxy-2,2,3,3,4,4-hexafluoropentoxy) biphenyl S-4'- (4- (2-Methoxybutoxy) phenyl) benzoate (Compound 21, Table 1)

301 mg (0,737 retool) of 4-(5-ethoxy-2,2,3,3,4,4-hexafluoropentoxy)-4'-hydroxybiphenyl (prepared essentially as in Example 11), 5 ml of methylene chloride, and 2 ml (approximately 1.5 g) of triethylamine were placed in a vial. 210 mg (1 eq) of S-4'-(4-(2-methylbutoxy)-phenyl)benzoic acid was weighed in a 15 ml flask and was refluxed for 15 minutes with 1 ml (approximately 1.6 g) of thionyl chloride to form the benzoyl chloride. Most of the excess unreacted thionyl chloride was removed by distillation, and the last traces were removed by heating under a nitrogen flow. The hydroxybiphenyl solution was added to the crude acid chloride, and the mixture was allowed to react for 15 minutes. A fine precipitate formed, so the mixture was diluted with methylene chloride to a total volume of about 10 ml, was washed once with water made acidic by the addition of a small amount of acetic acid, then was washed with a saturated aqueous sodium chloride solution. The purified organic phase was dried over anhydrous magnesium sulfate and was passed through a short column containing 2 g of silica gel, using methylene chloride as eluent. Solvent was removed and the product was recrystallized from about 30 ml of hot ethanol to give 245 mg (49.3% yield) of 4-(5-ethoxy-2,2,3,3,4,4-hexafluoropentoxy)biphenyl S-4'-(4-(2methoxybutoxy)-phenyl)benzoate.

Example 36

Preparation of 4-(5-Ethoxy-2,2,3,3,4,4-hexafluoropentoxy)biphenyl S-4'-(4-methylhexyloxy)benzoate (Compound 22, Table 1)

307 mg (0.737 mmol) of 4-(5-ethoxy-2,2,3,3,4,4-hexafluoropentoxy)-4,-hydroxybiphenyl (prepared essentially as in Example 11), 5 ml of methylene chloride, and 2 ml (approximately 1.5 g) of triethylamine were placed in a vial. 179 mg (1 eq) of S-4'-(4-methylhexoxy)benzoic acid was weighed in a 15 ml flask and was refluxed for 15 minutes with 1 ml (approximately 1.6 g) of thionyl chloride to form the benzoyl chloride. Most of the excess unreacted thionyl chloride was removed by distillation, and the last traces were removed by heating under a nitrogen flow. The hydroxybiphenyl solution was added to the crude acid chloride, and the mixture was allowed to react for 15 minutes. The organic solution of product was washed once with water made acidic by the addition of a small amount of acetic acid, then was washed with a saturated aqueous sodium chloride solution. The purified organic phase was dried over anhydrous magnesium sulfate and was passed through a short column containing 2 g of silica gel, using methylene chloride as eluent. Solvent was removed and the product was recrystallized from about 5 ml of hot methanol to give 200 mg (45% yield) of 4-(5-ethoxy-2,2,3,3,4,4-hexafluoropentoxy)biphenyl S-4'-(4-methylhexyloxy)benzoate.

Example 37

Preparation of 4'-(2,2,3,3,4,4-Hexafluoro-5-butoxypentoxy)-4-(S-2-chloropropanoyloxy)biphenyl (Compound 23, Table 1)

0.73 ml of a solution of oxalyl chloride (2M in $CH_2Cl_2$) was added by syringe to a solution of 0.144 g (1.33 mmol) of S-2-chloropropanoic acid in 2 ml $CH_2Cl_2$. A small drop of N,N-dimethylformamide was added and the solution was stirred under a nitrogen atmosphere until evolution of gases ceased. This solution was then added by syringe to a mixture of 0.5 g (1.14 mmol) of 4'-(2,2,3,3,4,4-hexafluoro-5-butoxypentoxy)-4-hydroxybiphenyl (prepared essentially as in Example 6), 0.43 ml of pyridine and 2 ml of $CH_2Cl_2$. The reaction mixture was stirred for 2 hours at room temperature, then filtered through a short pad of silica gel and washed through the gel with ethyl acetate. The filtrate was concentrated and the product was isolated by chromatography to give the desired product, 4'-(2,2,3,3,4,4-hexafluoro-5-butoxypentoxy)-4-(S-2-chloropropanoyloxy)biphenyl, as a white solid (0.422 g, 70% yield).

Example 38

Preparation of 4,-(2,2,3,3,4,4-Hexafluoro-5-butoxypentoxy)-4-hydroxybiphenyl S-2-Chloro-4-methylpentanoate (Compound 24, Table 1)

Compound 24 was prepared by esterification of S-2-chloro-4-methylpentanoic acid with 4'-(2,2,3,3,4,4-hexafluoro-5-butoxypentoxy)-4-hydroxybiphenyl (prepared essentially as in Example 6) essentially as described in Example 37.

Example 39

Preparation of 4'-(2,2,3,3,4,4-Hexafluoro-5-butoxypentoxy)-4-hydroxybiphenyl S-2-Fluoropentanoate (Compound 25, Table 1)

Compound 25 was prepared by esterification of S-2-fluoropentanoic acid with 4'-(2,2,3,3,4,4-hexafluoro-5-butoxypentoxy)-4-hydroxybiphenyl (prepared essentially as in Example 6) essentially as described in Example 37.

Example 40

Preparation of 4'-(2,2,3,3,4,4-Hexafluoro-5-butoxypentoxy)-4-(S-2-chloropropoxy)biphenyl (Compound 26, Table 1)

Compound 26 was prepared by etherification of S-1-p-toluenesulfonoxy-2-chloropropane acid with 4'-(2,2,3,3,4,4-hexafluoro-5-butoxypentoxy)-4-hydroxybiphenyl (prepared essentially as in Example 6) essentially as described in Example 6. The product was purified by chromatography on silica gel.

Example 41

Preparation of 4'-(2,2,3,3,4,4-Hexafluoro-5-ethoxypentoxy)-4-hydroxybiphenyl S-2-Chloropropionate (Compound 27, Table 1)

Compound 27 was prepared by esterification of S-2-chloropropionic acid with 4'-(2,2,3,3,4,4-hexafluoro-5-ethoxypentoxy)-4-hydroxybiphenyl (prepared essentially as in Example 11) essentially as described in Example 37.

Example 42

Preparation of 2-(2,2,3,3,4,4-Hexafluoro-5-ethoxypentoxy)-6-hydroxynapthalene 8-2-Chloropropionate (Compound 28, Table 1)

Compound 28 was prepared by esterification of S-2-chloropropionic acid with 2-(2,2,3,3,4,4-hexafluoro-5-ethoxypentoxy)-6-hydroxynapthalene (prepared essentially as in Example 7) essentially as described in Example 37.

Example 43

Preparation of 4-Hydroxyphenyl-(4-(5-butoxy-2,2,3,3,4,4-hexafluoropentoxy)benzoate S-2-Chloropropionate (Compound 29, Table 1)

Compound 29 was prepared by esterification of S-2-chloropropionic acid with 4-hydroxyphenyl-(4-(5-butoxy-2,2,3,3,4,4-hexafluoropentoxy)benzoate (prepared essentially as in Example 12) essentially as described in Example 37.

Example 44

Preparation of 5-(5-Butoxy-2,2,3,3,4,4-hexafluoropentoxy)-2-(4-hydroxyphenyl)pyrimidine S-2Chloropropionate (Compound 30, Table 1)

Compound 30 was prepared by esterification of S-2-chloropropionic acid with 5-(5-butoxy-2,2,3,3,4,4-hexafluoropentoxy)-2-(4-hydroxyphenyl)pyrimidine (prepared essentially as in Example 13) essentially as described in Example 37.

TABLE 1
| Compound No. | Structure |
|---|---|
| 1 | 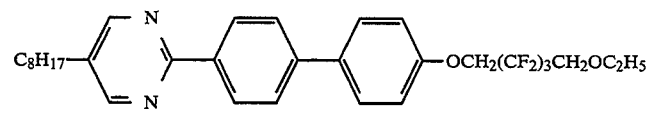 |
| 2 | 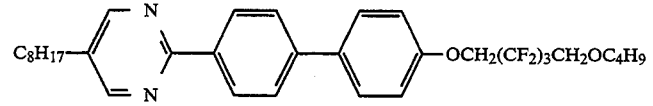 |
| 3 | 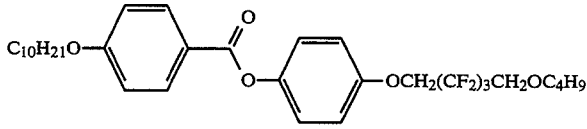 |
| 4 | 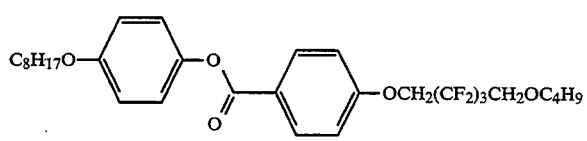 |
| 5 | 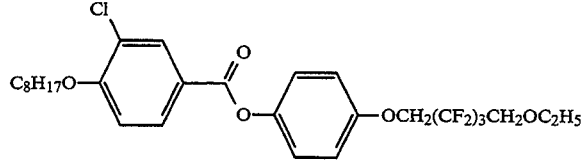 |
| 6 | 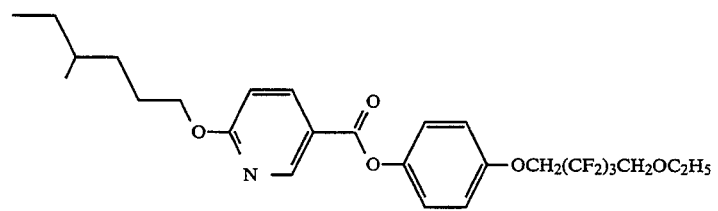 |
| 7 | 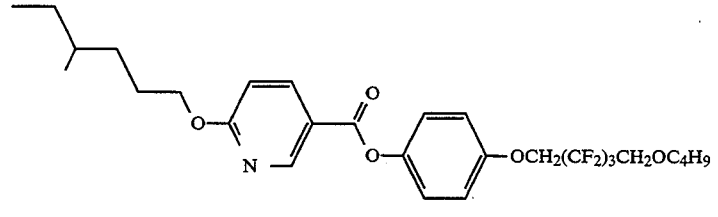 |
| 8 | 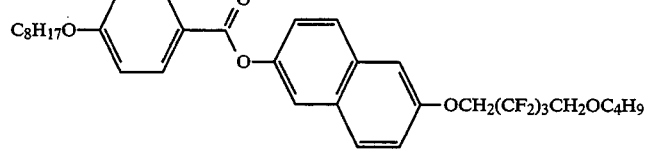 |
| 9 | 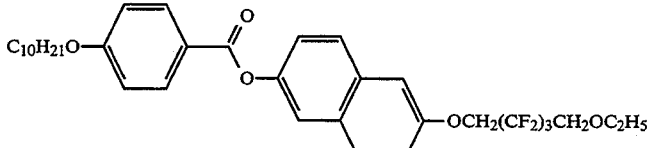 |

TABLE 1-continued

| Compound No. | Structure |
|---|---|
| 10 | $C_8H_{17}O$—[benzoate]—[biphenyl]—$OCH_2(CF_2)_3CH_2OC_2H_5$ |
| 11 | $C_5H_{11}$—[cyclohexyl-C(O)O]—[phenyl]—[OC(O)-phenyl]—$OCH_2(CF_2)_3CH_2OC_4H_9$ |
| 12 | $C_{10}H_{21}$—[pyrimidine]—[phenyl]—$OCH_2(CF_2)_3CH_2OC_2H_5$ |
| 13 | $C_{10}H_{21}$—[pyrimidine]—[phenyl]—$OCH_2CF_2(OCF_2CF_2)_2CF_2CH_2OC_2H_5$ |
| 14 | $C_{10}H_{21}$—[pyrimidine]—[phenyl]—$OCH_2(CF_2)_4CH_2OC_2H_5$ |
| 15 | $C_4H_9$—[pyrimidine]—[phenyl]—$OCH_2(CF_2)_3CH_2OCH_3$ |
| 16 | $C_8H_{17}$—[pyrimidine]—[phenyl]—$OCH_2(CF_2)_3CH_2OCH_3$ |
| 17 | $C_{10}H_{21}$—[pyrimidine]—[phenyl]—$OCH_2(CF_2)_3CH_2OCH_3$ |
| 18 | $C_8H_{17}$—[pyrimidine]—[phenyl]—$OCH_2(CF_2)_3CH_2OC_4H_9$ |
| 19 | $C_{10}H_{21}$—[pyrimidine]—[phenyl]—$OCH_2(CF_2)_3CH_2OC_4H_9$ |
| 20 | $C_4H_9$—[pyrimidine]—[phenyl]—$OCH_2(CF_2)_3CH_2OC_4H_9$ |
| 21 | (S)-2-methylbutyl-O—[biphenyl]—C(O)O—[biphenyl]—$OCH_2(CF_2)_3CH_2OC_2H_5$ |

TABLE 1-continued

| Compound No. | Structure |
|---|---|
| 22 | 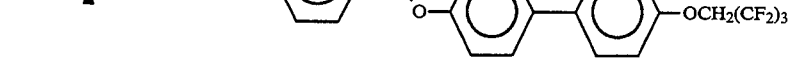 |
| 23 | 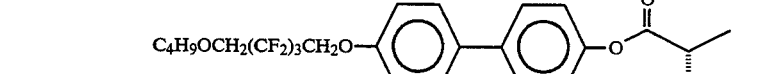 |
| 24 | 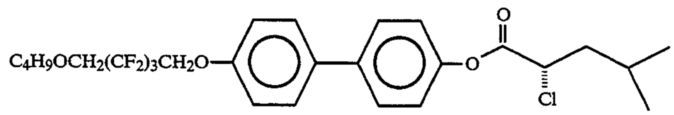 |
| 25 | 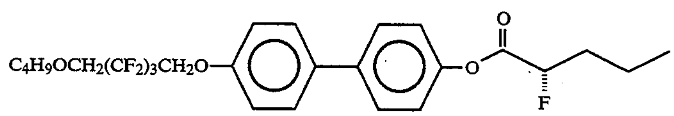 |
| 26 | 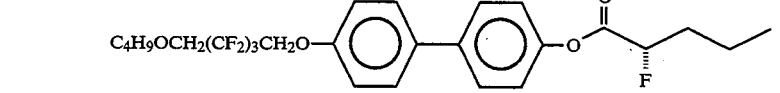 |
| 27 | 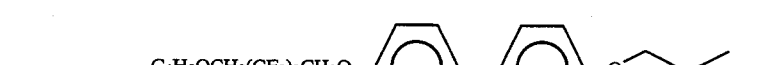 |
| 28 | 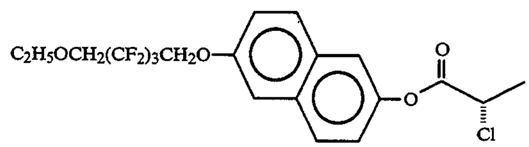 |
| 29 | 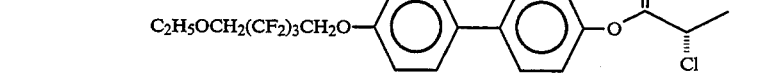 |
| 30 | 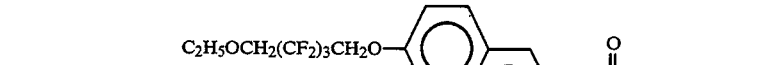 |

The compounds of Table 1 were evaluated for transition temperatures by optical observation of material phase changes using a Linkam TMH600 hot stage and a Zeiss polarizing microscope. The transition temperatures (°C.) were obtained upon cooling from the isotropic state (I) and are set forth in Table 2.

TABLE 2

Mesophase Characterization for Compounds Listed in Table 1

| Compound No. | I to N | to $S_A$ | to $S_C$ | to M | to K |
|---|---|---|---|---|---|
| 1 | — | 157 | — | 51 | |
| 2 | — | 135 | — | 83 | |
| 3 | — | 41 | 21 | 15 | |
| 4 | — | — | — | mp = 49 | |
| 5 | — | — | — | 38 | |
| 6 | — | I < −24 | — | — | |
| 7 | — | I < −20 | — | — | |
| 8 | — | 69 | — | 28 | |
| 9 | — | 79 | — | 41 | |
| 10 | 126 | 120 | 71 | 25 | |
| 11 | 118 | 87 | 72 | 63 | 36 |
| 12 | — | — | — | — | I < −20 |
| 13 | — | — | — | −3.8 | −11.2 |
| 14 | — | — | — | — | I < −20 |
| 15 | — | — | — | — | I < −20 |
| 16 | — | 26 | — | −15 | |

TABLE 2-continued

Mesophase Characterization for Compounds Listed in Table 1

| Compound No. | I to N | to $S_A$ | to $S_C$ | to M | to K |
|---|---|---|---|---|---|
| 17 | — | 28 | — | 1 | |
| 18 | — | 5 | — | −20 | |
| 19 | — | 4 | — | −3 | |
| 20 | — | — | — | — | I < −20 |
| 21 | — | 242 | — | | 162 |
| 22 | — | — | — | 136.6 | 120.3 |
| 23 | — | — | — | — | 54.5 |
| 24 | — | — | — | — | I < −10 |
| 25 | — | 41 | — | 37 | 1.1 |
| 26 | — | — | — | 18.7 | |
| 27 | — | — | — | 63.9 | |
| 28 | — | — | — | — | I < −20 |
| 29 | — | — | — | 18.9 | |
| 30 | — | — | — | — | mp = 45° C. |

N = Nematic,
$S_A$ = Smectic A,
$S_C$ = Smectic C,
M = Higher order mesophase,
K = Crystalline

Comparative Examples 1-6

Comparative Mesophase Characterization of Liquid Crystal Compounds

Table 3 compares the temperatures (in degrees centigrade) of the $S_A \rightarrow S_C$ and $S_C \rightarrow M(K)$ transitions of the compounds of this invention with those of other liquid crystal compounds (compounds C1-C6). The mesophase characterization was obtained by optical microscopy during the cooling cycle (5 deg/min). The data indicates that the compounds of the invention have lower transition temperatures than do the other liquid crystal compounds.

TABLE 3

Mesophase Characterization of Liquid Crystal Compounds

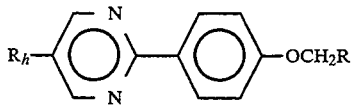

| Comp. No. | $R_h$ | R | I to $S_A$ | to $S_C$ | to M (K) |
|---|---|---|---|---|---|
| C1 | $C_{10}H_{21}$— | $C_5F_{11}$— | 84 | 73 | 47 |
| C2 | $C_{10}H_{21}$— | $C_5H_{11}$— | 66 | 49 | 29 |
| C3 | $C_8H_{17}$— | $C_3H_7$— | 73 | 53 | 34 |
| C4 | $C_8H_{17}$— | $CF_3CF_2OCF_2$— | 67 | 26 | 7 |
| C5 | $C_8H_{17}$— | $C_4F_9OCF_2CF_2OCF_2$— | 74 | 50 | −5 |
| C6 | $C_8H_{17}$— | $C_4H_9OCH_2CH_2OCH_2$— | — | — | mp = 54° C. |
| 18 | $C_8H_{17}$— | $CH_3(CH_2)_3OCH_2(CF_2)_3$— | 5 | — | −20 |
| 19 | $C_{10}H_{21}$— | $CH_3(CH_2)_3OCH_2(CF_2)_3$— | 4 | — | −3 |
| 16 | $C_8H_{17}$— | $CH_3OCH_2(CF_2)_3$— | 26 | — | −15 |
| 17 | $C_{10}H_{21}$— | $CH_3OCH_2(CF_2)_3$— | 28 | — | 1 |

Example 45 describes a liquid crystal compound mixture of this invention.

Example 45 and Comparative Example 7
Transition Temperature Lowering Effect of the Compounds of the Invention in Admixture With Other Liquid Crystal compounds A mixture of liquid crystal compounds was prepared, and its composition is shown in Table 4 (components are listed in parts by weight).

TABLE 4

Liquid Crystal Compound Mixture C7
(Comparative Example 7)

| | |
|---|---|
| 2-[4-(1,1-Dihydroperfluorohexyloxy)]phenyl-5-octylpyrimidine | 50 |

TABLE 4-continued

Liquid Crystal Compound Mixture C7
(Comparative Example 7)

| | |
|---|---|
| 2-[4-(1,1-Dihydroperfluorohexyloxy)]phenyl-5-nonylpyrimidine | 50 |
| 2-[4-(1,1-Dihydroperfluorohexyloxy)]phenyl-5-decylpyrimidine | 50 |
| 2-[4-(1,1-Dihydroperfluorobutoxy)]phenyl-5-octylpyrimidine | 20 |
| 2-[4-(1,1-Dihydroperfluorobutoxy)]phenyl-5-decylpyrimidine | 20 |
| 2-[4-(1,1-Dihydro-2-(2-perfluorobutoxyperfluoroethoxy)-perfluoroethoxy)]phenyl-5-hexylpyrimidine | 30 |
| 2-[4-(1,1-Dihydroperfluorooctyloxy)]phenyl-5-hexylpyrimidine | 20 |
| 2-[4-(1,1-Dihydroperfluorooctyloxy)]phenyl-5-septylpyrimidine | 20 |
| 2-[4-(1,1-Dihydroperfluorooctyloxy)]phenyl-5-octylpyrimidine | 20 |
| 2-[4-(1,1-Dihydroperfluorooctyloxy)]phenyl-5-nonylpyrimidine | 20 |
| 2-[4-(1,1-Dihydroperfluorooctyloxy)]phenyl-5-decylpyrimidine | 20 |
| TOTAL | 320 |

The phase transition temperatures for this comparative mixture were measured essentially as described above for Table 2 and found to be:

When 5-decyl-2-[4-(2,2,3,3,4,4-hexafluoro-5-butoxypentoxy)]-phenyl-pyrimidine (Compound 19, Table 1) was admixed at the level of 48 parts by weight to 320 parts by weight of the mixture listed in Table 4 (to give Example 45 of the invention), the following transition temperatures were observed (using the same technique as that described above):

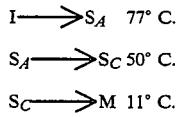

I ⟶ $S_A$ 77° C.

$S_A$ ⟶ $S_C$ 50° C.

$S_C$ ⟶ M 11° C.

This comparison demonstrates the transition temperature lowering effect that the compounds of this invention have on mixtures of other liquid crystal compounds.

Example 46 describes a liquid crystal display device of this invention.

Example 46

A device utilizing a chiral compound (Compound 25) of this invention was constructed as follows. Two indium-tin oxide (ITO) coated glass plates (1.09 mm thick, 300 Å ITO coating) were used. A photoresist was coated on one of the plates and was exposed through a circular holed mask until developed, resulting in photoresist posts of approximately 1.5 microns in height. These posts served as spacers for the assembled device and determined the liquid crystal fill gap between the two plates. The non-posted plate was coated with a solution of nylon 6/6 in formic acid and the posted plate was coated with an insulating layer (Owens-Illinois GR651L). The nylon 6/6 coated plate was unidirectionaly rubbed with a 65% cotton / 35% rayon fabric. The two plates were glued together using a UV curable adhesive. The cell gap created was then filled with the following mixture:

13.5 wt%

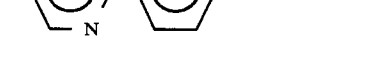

C$_6$H$_{13}$— ... —OCH$_2$CF$_2$OC$_2$F$_4$OC$_4$F$_9$ 22.6 wt%

C$_8$H$_{17}$— ... —OCH$_2$C$_5$F$_{11}$ 22.5 wt%

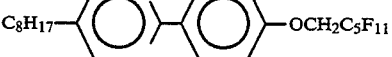

C$_9$H$_{19}$— ... —OCH$_2$C$_5$F$_{11}$ 22.6 wt%

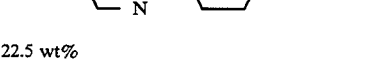

C$_{10}$H$_{21}$— ... —OCH$_2$C$_5$F$_{11}$ 9.0 wt%

C$_9$H$_{19}$— ... —OCH$_2$C$_3$F$_7$ 9.8 wt%

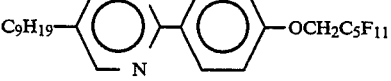

C$_4$H$_9$OCH$_2$(CF$_2$)$_3$CH$_2$O— ...

The phase transition temperatures for the mixture were measured essentially as described above for Table 2 and found to be:

| | |
|---|---|
| I to S$_A$ | 80.3° C. |
| S$_A$ to S$_C$ | 50.4° C. |
| S$_C$ to M | 20.5° C. |

The response time was measured at the rising edge of the cell photoresponse and calculated from 10–90% of the maximum transmission. The response time, measured using a photodetector, with a field of 9.5 V/μ and a temperature of 28.3° C., was 10.3 μs. The polarization was determined as described in Miyasato et al., Jap. J. Appl. Phys. b 22, 661 (1983) to be 20.2 nC/cm² at 28.3° C.

Various modifications and alterations of this invention will become apparent to those skilled in the art without departing from the scope and spirit of this invention.

We claim:

1. Fluorine-containing, chiral and achiral liquid crystal compounds having smectic mesophases or latent smectic mesophases, the compounds comprising (a) an aliphatic fluorocarbon terminal portion comprising a perfluorinated alkylene group and a terminal hydrocarbon alkyl group, said groups optionally containing at least one catenary ether oxygen atom; (b) an aliphatic hydrocarbon terminal portion; and (c) a central core connecting said terminal portions.

2. The compounds of claim 1 wherein said aliphatic fluorocarbon terminal portion is represented by the formula —D—R$_f$—R$_h$, wherein D is selected from the group consisting of a covalent bond, $$-\underset{\underset{O}{\|}}{C}-O-C_rH_{2r}-,\ -O-C_rH_{2r}-,$$

$$-O(C_sH_{2s}O)_tC_rH_{2r}-,\ -C_rH_{2r}-,$$

$$(C_sH_{2s}O)_tC_rH_{2r}-,\ -OSO_2-,\ -SO_2-,$$

$$-SO_2-C_rH_{2r}-,\ -C_rH_{2r}-\underset{\underset{C_pH_{2p+1}}{|}}{N}-SO_2-,$$

$$-C\equiv C-,\ -CH=CH-,\ -\underset{\underset{O}{\|}}{C}-,$$

$$-O-\underset{\underset{O}{\|}}{C}-C_rH_{2r}-,\ -C_rH_{2r}-\underset{\underset{C_pH_{2p+1}}{|}}{N}-\underset{\underset{O}{\|}}{C}-,$$

and combinations thereof, where r and r' are independently integers of 1 to about 20, s is independently an integer of 1 to about 10 for each (C$_s$H$_{2d}$O), t is an integer of 1 to about 6, and p is an integer of 0 to about 4; R$_f$ is a linear or branched, perfluorinated alkylene group having from 1 to about 10 carbon atoms and optionally containing one or more catenary ether oxygen atoms; and R$_h$ is a linear or branched alkyl group having from 1 to about 14 carbon atoms and optionally containing one or more catenary ether oxygen atoms.

3. The compounds of claim 2 wherein said R$_f$ is a linear perfluoroalkylene group having from about 2 to about 6 carbon atoms; said R$_h$ is a linear alkyl group having from about 3 to about 10 carbon atoms; and at least one of the groups R$_h$ and R$_r$ contains at least one catenary ether oxygen atom.

4. The fluorine-containing, achiral liquid crystal compounds of claim 1 wherein said compounds are represented by the general formula (I):

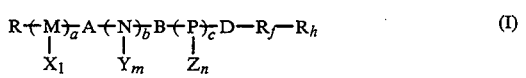

where M, N, and P are each independently selected from the group consisting of

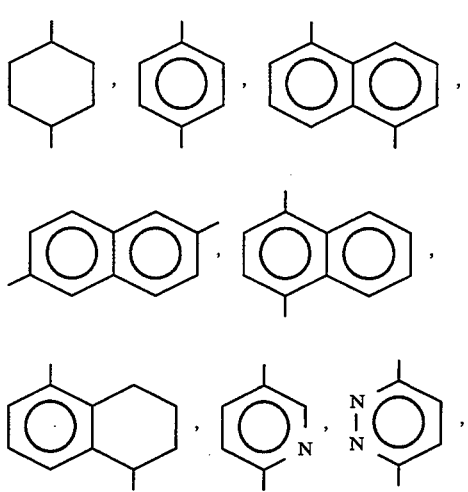

-continued

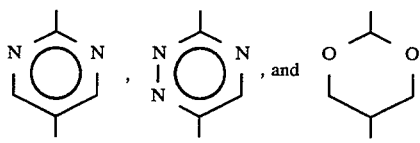

a, b, and c are each independently zero or an integer of from 1 to 3, with the proviso that the sum of a+b+c be at least 1;
each A and B are non-directionally and independently selected from the group consisting of a covalent bond,

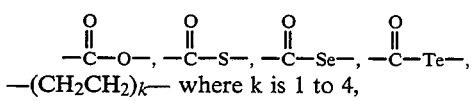

—(CH$_2$CH$_2$)$_k$— where k is 1 to 4,

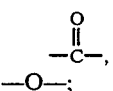

—O—;

each X, Y, and Z are independently selected from the group consisting of —H, —Cl, —F, —Br, —I, —OH, —OCH$_3$, —CH$_3$, —CF$_3$, —OCF$_3$ —CN, and —NO$_2$;
each l, m, and n are independently zero or an integer of 1 to 4;
D is selected from the group consisting of a covalent bond,

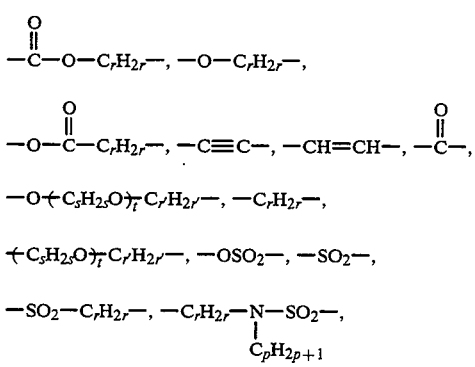

and combinations thereof where r and r' are independently integers of 1 to about 20, s is independently an integer of 1 to about 10 for each (C$_s$H$_{2s}$O), t is an integer of 1 to about 6, and p is an integer of 0 to about 4;
R is selected from the group consisting of —O$\leftarrow$C$_q$H$_{2q}$—O$\rightarrow_w$C$_{q'}$H$_{2q'+1}$, $\leftarrow$C$_q$H$_{2q}$—O$\rightarrow_w$C$_{q'}$H$_{2q'+1}$, —C$_q$H$_{2q}$—R', —O—C$_q$H$_{2q}$—R', —C(=O)—O—C$_q$H$_{2q}$—R', and —O—C(=O)—C$_q$H$_{2q}$—R', where R' is selected from the group consisting of —Cl, —F, —CF$_3$, —NO$_2$, —CN, —H,

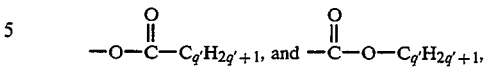

where q and q' are independently integers of 1 to about 20, w is an integer of 1 to about 10, and R can be linear or branched;
R$_f$ is a linear or branched, perfluorinated alkylene group having from 1 to about 10 carbon atoms and optionally containing one or more catenary ether oxygen atoms; and R$_h$ is a linear or branched alkyl group having from 1 to about 14 carbon atoms and optionally containing one or more catenary ether oxygen atoms.

5. The compounds of claim 4 wherein said R$_f$ is a linear perfluoroalkylene group having from about 2 to about 6 carbon atoms; said R$_h$ is a linear alkyl group having from about 3 to about 10 carbon atoms; and at least one of the groups R$_h$ and R$_f$ contains at least one catenary ether oxygen atom.

6. The fluorine-containing, chiral liquid crystal compounds of claim 1 wherein said compounds are represented by the general formula (I):

$$R\text{-}(M)_a\text{-}A\text{-}(N)_b\text{-}B\text{-}(P)_c\text{-}D\text{-}R_f\text{-}R_h \quad (I)$$
$$\quad\quad X_l \quad\quad Y_m \quad\quad Z_n$$

where M, N, and P are each independently selected from the group consisting of

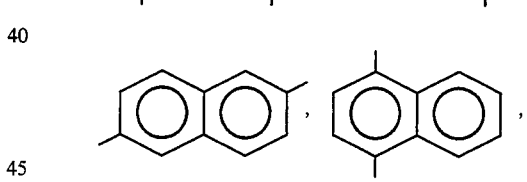

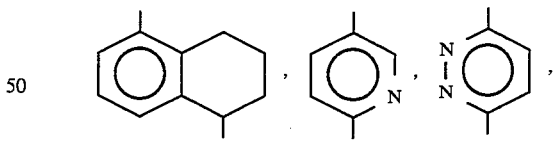

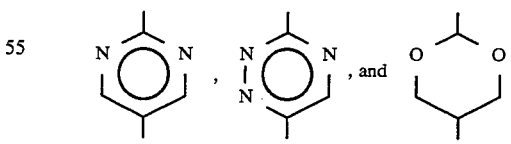

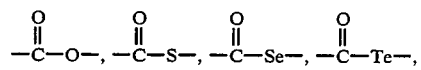

a, b, and c are each independently zero or an integer of from 1 to 3, with the proviso that the sum of a+b+c be at least 1;
each A and B are non-directionally and independently selected from the group consisting of a covalent bond, —C(=O)—O—, —C(=O)—S—, —C(=O)—Se—, —C(=O)—Te—, —$(CH_2CH_2)_k$— where k is 1 to 4, —CH=CH—, —C≡C—, —CH=N—, —CH$_2$—O—,

and —O—;

each X, Y, and Z are independently selected from the group consisting of —H, —Cl, —F, —Br, —I, —H, OCH$_3$, —CH$_3$, —CF$_3$, —OCF$_3$ —CN, and —NO$_2$;

each l, m, and n are independently zero or an integer of 1 to 4;

D is selected from the group consisting of a covalent bond,

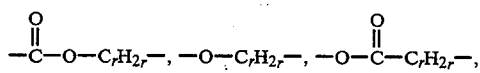

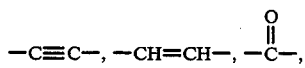

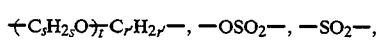

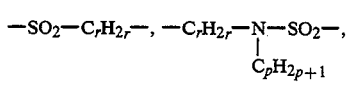

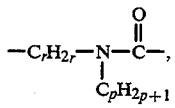

and combinations thereof, where r and r' are independently integers of 1 to about 20, s is independently an integer of 1 to about 10 for each ($C_sH_{2s}O$), t is an integer of 1 to about 6, and p is an integer of 0 to about 4;

R is selected from the group consisting of

—O$(C_qH_{2q}$—O$)_wC_{q'}H_{2q'+1}$, —$(C_qH_{2q}$—O$)_wC_{q'}H_{2'+1}$,

—$C_qH_{2q}$—R', —O—$C_qH_{2q}$—R', 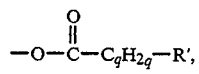

and

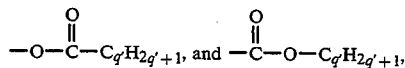

where R' is selected from the group consisting of —Cl, —F, —CF$_3$, —NO$_2$, —CN, —H, —O—$\overset{O}{\overset{\|}{C}}$—$C_{q'}H_{2q'+1}$, and —$\overset{O}{\overset{\|}{C}}$—O—$C_{q'}H_{2q'+1}$, where q and q' are independently integers of 1 to about 20, w is an integer of 1 to about 10, and R can be linear or branched, with the proviso that R is chiral;

$R_f$ is a linear or branched, perfluorinated alkylene group having from 1 to about 10 carbon atoms and optionally containing one or more catenary ether oxygen atoms; and $R_h$ is a linear or branched alkyl group having from 1 to about 14 carbon atoms and optionally containing one or more catenary ether oxygen atoms.

7. The compounds of claim 6 wherein said $R_f$ is a linear perfluoroalkylene group having from about 2 to about 6 carbon atoms; said $R_h$ is a linear alkyl group having from about 3 to about 10 carbon atoms; and at least one of the groups $R_h$ and $R_f$ contains at least one catenary ether oxygen atom.

8. The compounds represented by the formula

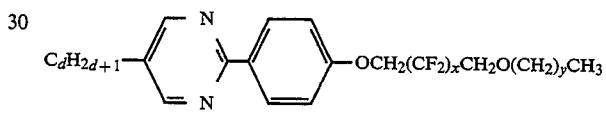

where d is an integer of about 4 to about 10, x is an integer of 1 to about 10, and y is an integer of 1 to about 12.

9. The compounds represented by the formula

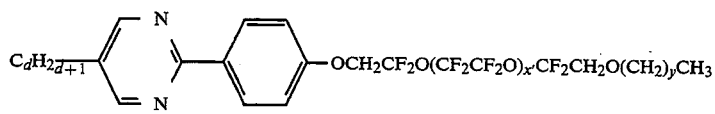

where d is an integer of about 4 to about 10, x is an integer of 1 to about 10, and y is an integer of 1 to about 12.

10. The compounds represented by the formula

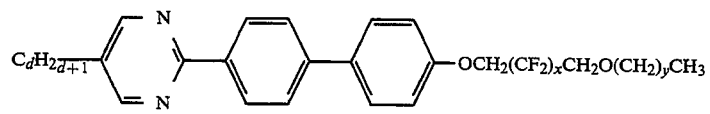

where d is an integer of about 4 to about 10, x is an integer of 1 to about 10, and y is an integer of 1 to about 12.

11. The compounds represented by the formula

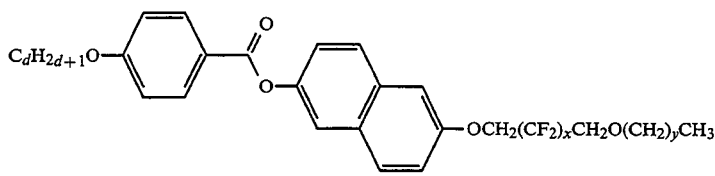

where d is an integer of about 4 to about 10, x is an integer of 1 to about 10, and y is an integer of 1 to about 12.

12. The compounds represented by the formula

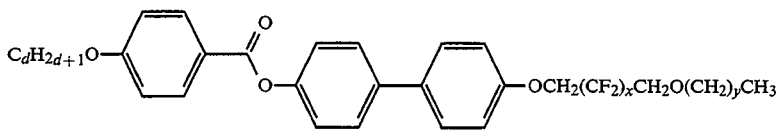

where d is an integer of about 4 to about 10, x is an integer of 1 to about 10, and y is an integer of 1 to about 12.

13. The compounds represented by the formula

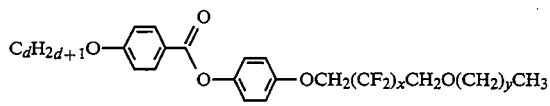

where d is an integer of about 4 to about 10, x is an integer of 1 to about 10, and y is an integer of 1 to about 12.

14. The compounds represented by the formula

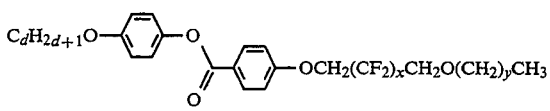

where d is an integer of about 4 to about 10, x is an integer of 1 to about 10, and y is an integer of 1 to about 12.

15. The compounds represented by the formula

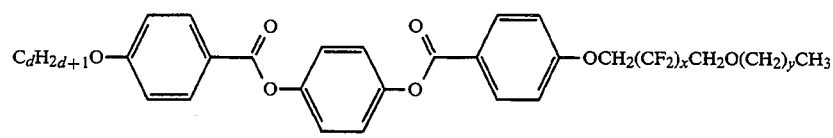

where d is an integer of about 4 to about 10, x is an integer of 1 to about 10, and y is an integer of 1 to about 12.

16. The compounds represented by the formula

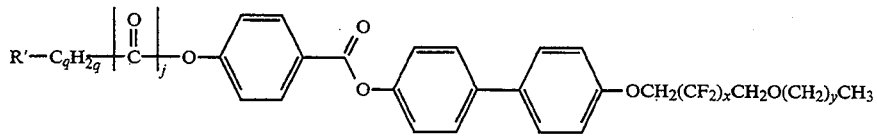

where x is an integer of 1 to about 10; y is an integer of 1 to about 12; j is an integer of 0 or 1; said q is an integer of 2 to about 10; said R' is selected from the group consisting of hydrogen, fluorine, chlorine, and perfluoromethyl; and said $C_qH_{2q}$ is linear or branched.

17. The compounds represented by the formula

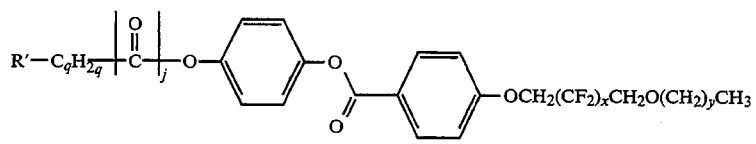

where x is an integer of 1 to about 10; y is an integer of 1 to about 12; j is an integer of 0 or 1; said q is an integer of 2 to about 10; said R' is selected from the group consisting of hydrogen, fluorine, chlorine, and perfluoromethyl; and said $C_qH_{2q}$ is linear or branched.

18. The compounds represented by the formula

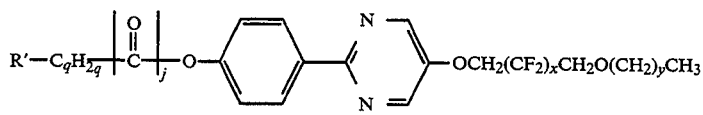

where x is an integer of 1 to about 10; y is an integer of 1 to about 12; j is an integer of 0 or 1; said q is an integer of 2 to about 10; said R' is selected from the group consisting of hydrogen, fluorine, chlorine, and perfluoromethyl; and said $C_qH_{2q}$ is linear or branched.

19. The compounds represented by the formula

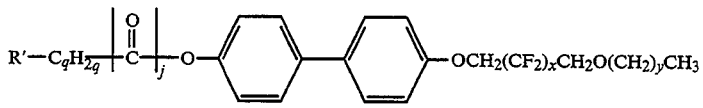

where x is an integer of 1 to about 10; y is an integer of 1 to about 12; j is an integer of 0 or 1; said q is an integer of 2 to about 10; said R' is selected from the group consisting of hydrogen, fluorine, chlorine, and perfluoromethyl; and said $C_qH_{2q}$ is linear or branched.

20. The compounds represented by the formula

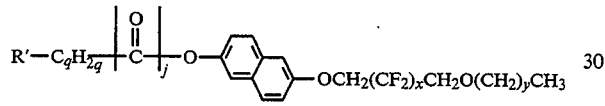

where x is an integer of 1 to about 10; y is an integer of 1 to about 12; j is an integer of 0 or 1; said q is an integer of 2 to about 10; said R' is selected from the group consisting of hydrogen, fluorine, chlorine, and perfluoromethyl; and said $C_qH_{2q}$ is linear or branched.

21. The compounds represented by the formula

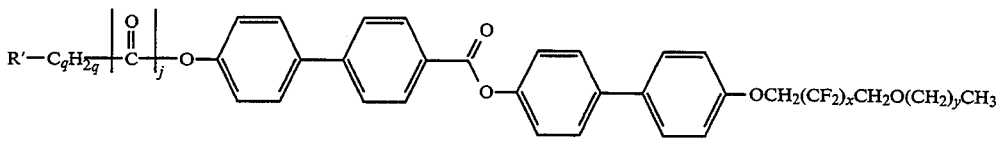

where x is an integer of 1 to about 10; y is an integer of 1 to about 12; j is an integer of 0 or 1; said q is an integer of 2 to about 10; said R' is selected from the group consisting of hydrogen, fluorine, chlorine, and perfluoromethyl; and said $C_qH_{2q}$ is linear or branched.

22. A mixture of liquid crystal compounds comprising at least one fluorine-containing liquid crystal compound of claim 1.

23. A liquid crystal display device containing at least one fluorine-containing liquid crystal compound of claim 1.

24. Fluorine-containing intermediate compounds represented by the general formula

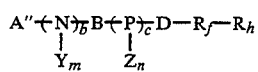

where N and P are each independently selected from the group consisting of

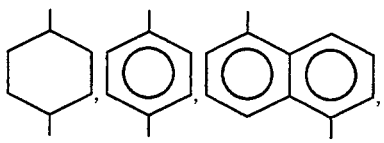

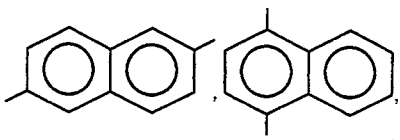

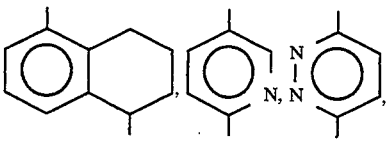

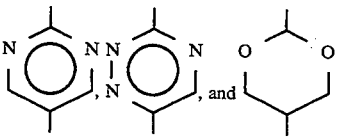

b and c are each independently zero or an integer of from 1 to 3; B is non-directionally selected from the group consisting of a covalent bond,

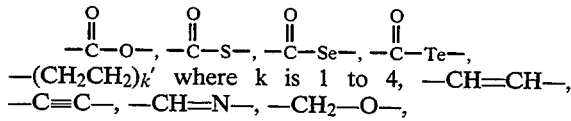

$—(CH_2CH_2)_{k'}$ where k is 1 to 4, $—CH=CH—$, $—C\equiv C—$, $—CH=N—$, $—CH_2—O—$, $$-\overset{O}{\underset{\|}{C}}-,$$

and —O—; A" is selected from the group consisting of —OH, —COOH, —CH (CH$_2$OH)$_2$, —SH, —SeH, —the, —NH$_2$, —COCl, —CHO, —OSO$_2$R$_f'$, and —CH$_2$COOH, where R$_f'$ is a perfluoroalkyl group having from 1 to about 10 carbon atoms; Y and Z are independently selected from the group consisting of —H, —Cl, —F, —Br, —I, —OH, —OCH$_3$, —CH$_3$, —CF$_3$, —OCF$_3$, —CN, and —NO$_2$; m and n are independently zero or an integer of 1 to 4; D is selected from the group consisting of a covalent bond,

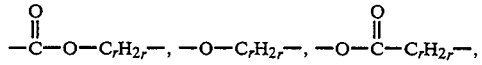

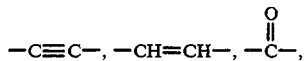

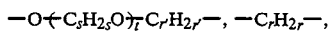

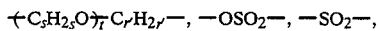

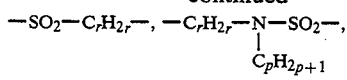

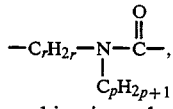

and combinations thereof, where r and r' are independently integers of 1 to about 20, s is independently an integer of 1 to about 10 for each (C$_s$H$_{2s}$O), t is an integer of 1 to about 6, and p is an integer of 0 to about 4; R$_f$ is a linear or branched, perfluorinated or partially-fluorinated alkylene group having from 1 to about 10 carbon atoms and optionally containing one or more catenary ether oxygen atoms; and R$_h$ is a linear or branched alkyl group having from 1 to about 14 carbon atoms and optionally containing one or more catenary ether oxygen atoms.

* * * * *

UNITED STATES PATENT AND TRADEMARK OFFICE
CERTIFICATE OF CORRECTION

PATENT NO.: 5,399,291
DATED: March 21, 1995
INVENTOR(S): Eugene P. Janulis, Gilbert C. Johnson, Marc D. Radcliffe, Patricia M. Savu, Daniel C. Snustad, and Terence D. Spawn It is certified that error appears in the above-identified patent and that said Letters Patent is hereby corrected as shown below:

Col. 5, line 10, delete " 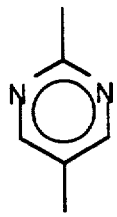 " and insert -- 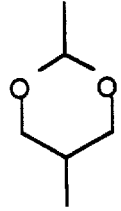 --.

Col. 5, line 31, delete "-C=C-" and insert -- -C≡C- --.

Col. 5, line 54, delete " 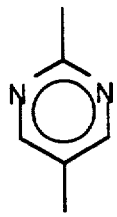 " and insert -- 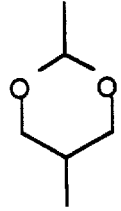 --.

Col. 9, line 47, delete "34" and insert --14--.

Col. 10, line 22, delete "And" and insert --And--.

Col. 11, line 40, delete " 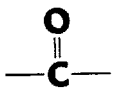 , and -O-" and insert

-- -CH=CH-, -C≡C-, -CH=N-, -CH$_2$-O-, -C-, and -O-; --.

UNITED STATES PATENT AND TRADEMARK OFFICE
CERTIFICATE OF CORRECTION

PATENT NO.: 5,399,291

DATED: March 21, 1995

INVENTOR(S): Eugene P. Janulis, Gilbert C. Johnson, Marc D. Radcliffe, Patricia M. Savu, Daniel C. Snustad, and Terence D. Spawn It is certified that error appears in the above-identified patent and that said Letters Patent is hereby corrected as shown below:

Col. 11, line 43, delete "-the," and insert -- -TeH, --.

Col. 11, line 67, delete " $-C_sH_{2s}O(C_{r'}H_{2r'})-$ , " and insert -- $-(C_sH_{2s}O)_tC_{r'}H_{2r'}-$ , --.

Col. 16, line 34, delete "H20" and insert --$H_2O$--.

Col 18, line 45, delete "(0,021" and insert --(0.021--.

Col. 19, line 52 and line 53, delete "rain)" and insert --min)--.

Col. 22, line 32, delete "?" and insert --7--.

Col. 22, line 66, delete "4,-(" and insert -- 4'-( --.

Col. 26, line 50, delete "S-4'-" and insert -- $\underline{S}$-4'- --.

Col. 26, line 52, delete "(0,737" and insert --(0.737--.

Col. 26, line 56, delete "S-4'-" and insert -- $\underline{S}$-4'- --.

UNITED STATES PATENT AND TRADEMARK OFFICE
CERTIFICATE OF CORRECTION

PATENT NO.: 5,399,291

DATED: March 21, 1995

INVENTOR(S): Eugene P. Janulis, Gilbert C. Johnson, Marc D. Radcliffe, Patricia M. Savu, Daniel C. Snustad, and Terence D. Spawn It is certified that error appears in the above-identified patent and that said Letters Patent is hereby corrected as shown below:

Col. 27, line 8, delete "S-4'-" and insert -- $\underline{S}$-4'- --.

Col. 27, line 16, delete "(0,737" and insert --(0.737--.

Col. 27, line 17, delete "-4," and insert -- -4' --.

Col. 28, line 41, delete "8-2" and insert -- $\underline{S}$-2 --.

Col. 36, line 27, after "be:" insert -- I ------> $S_A$     94°C
$S_A$ ------> $S_C$     67°C
$S_C$ ------> M     23°C--.

Col. 37, line 27, after "9.0 wt%", delete "$C_9H_{19}$" and insert -- $C_{10}H_{21}$ --.

Col. 38, line 25, delete "$(C_sH_{2d}O)$," and insert -- $(C_sH_{2s}O)$ --.

Col. 39, lines 22 and 23, delete "$-\overset{\overset{O}{\|}}{C}-$, -O-;" and insert -- -CH=CH-, -C≡C-, -CH=N-, -CH$_2$-O-, $-\overset{\overset{O}{\|}}{C}-$, and -O-; --.

UNITED STATES PATENT AND TRADEMARK OFFICE
CERTIFICATE OF CORRECTION

PATENT NO.: 5,399,291

DATED: March 21, 1995

INVENTOR(S): Eugene P. Janulis, Gilbert C. Johnson, Marc D. Radcliffe, Patricia M. Savu, Daniel C. Snustad, and Terence D. Spawn It is certified that error appears in the above-identified patent and that said Letters Patent is hereby corrected as shown below:

Col. 41, line 9, delete "-H," and insert -- -OH, --.

Col. 46, line 56, delete ")$_k$." and insert -- )$_k$- --.

Col. 46, line 64, delete "-the" and insert -- -TeH --.

Signed and Sealed this

Twenty-ninth Day of October 1996

Attest:

BRUCE LEHMAN

*Attesting Officer*    Commissioner of Patents and Trademarks